United States Patent [19]

Sit et al.

[11] Patent Number: 4,870,187
[45] Date of Patent: Sep. 26, 1989

[54] ANTIHYPERCHOLESTEROLEMIC TETRAZOL-1-YL COMPOUNDS

[75] Inventors: Sing-Yuen Sit, Meriden; John J. Wright, Guilford, both of Conn.

[73] Assignee: Bristol-Myers Company, New York, N.Y.

[21] Appl. No.: 235,355

[22] Filed: Aug. 23, 1988

[51] Int. Cl.$^4$ .......................................... C07D 257/04
[52] U.S. Cl. ................................... 548/253; 548/112
[58] Field of Search ......................... 548/253; 514/381

[56] References Cited

U.S. PATENT DOCUMENTS

| 3,278,381 | 10/1966 | Bossinger et al. | 514/381 |
| 4,054,666 | 10/1977 | Sellstedt | 514/381 |
| 4,621,009 | 11/1986 | Loev | 514/381 |

FOREIGN PATENT DOCUMENTS 0006584  9/1988  PCT Int'l Appl. ................ 548/253

Primary Examiner—David B. Springer
Attorney, Agent, or Firm—Aldo A. Algieri

[57] ABSTRACT

Compounds of the formula

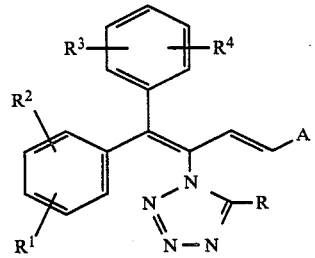

wherein
$R^1$, $R^2$, $R^3$, and $R^4$ each are independently hydrogen, halogen, $C_{1-4}$alkyl, $C_{1-4}$alkoxy or trifluoromethyl;
R is hydrogen, $C_{1-4}$alkyl or phenyl;
A is

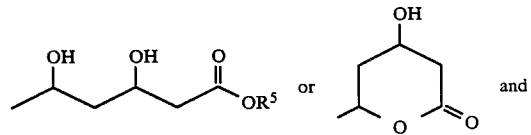

$R^5$ is hydrogen, a hydrolyzable ester group or a cation to form a non-toxic pharmaceutically acceptable salt, are novel antihypercholesterolemic agents which inhibit cholesterol biosynethesis. Intermediates and processes for their preparation are disclosed.

11 Claims, No Drawings

ANTIHYPERCHOLESTEROLEMIC TETRAZOL-1-YL COMPOUNDS

BACKGROUND OF THE INVENTION

1. Field of the Invention

The present invention provides novel tetrazol-1-yl compounds which are potent inhibitors of the enzyme 3-hydroxy-3-methylglutaryl coenzyme A (HMG-CoA) reductase and, therefore, are useful in the treatment or prevention of hypercholesterolemia, hyperlipoproteinemia and atherosclerosis. The present invention also provides novel processes for the preparation of the tetrazol-1-yl compounds and to certain intermediates in their preparation.

2. Disclosure Statement

The natural fermentation products Compactin (R=H) disclosed by A. Endo, et al. in *Journal of Antibiotics,* 29, 1346–1348 (1976) and Mevinolin (R=CH$_3$) disclosed by A. W. Alberts, et al. in *J. Proc. Natl. Acad. Sci. U.S.A.,* 77, 3957 (1980) are very active antihypercholesterolemic agents which limit cholesterol biosynthesis by inhibiting the enzyme HMG-CoA reductase, the rate-limiting enzyme and natural point of cholesterogenesis regulation in mammals, including man. Compactin (R=H) and Mevinolin (R=CH$_3$; also known as lovastatin) have the structures shown below:

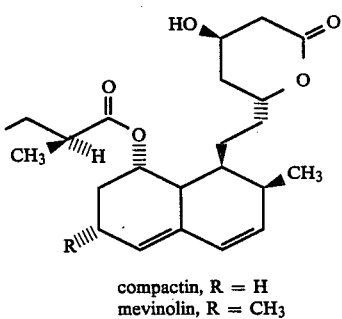

compactin, R = H
mevinolin, R = CH$_3$

A number of structurally related synthetic compounds useful in the treatment of hypercholesterolemia have also been disclosed in patents and other publications. The synthetic art most closely related is as follows:

U.S. Pat. No. 4,198,425, issued Apr. 15, 1980 to S. Mistui, et al. describes novel mevalonolactone derivatives useful for the treatment of hyperlipidemia and having the general formula

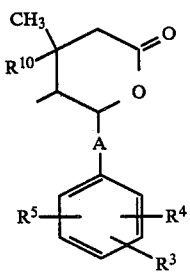

wherein A represents a direct linkage, methylene, ethylene, trimethylene or vinylene group and R$^3$, R$^4$ and R$^5$ represent various substituents.

International patent application WO 84/02131 published June 7, 1984 describes analogs of mevalonolactone having the structure

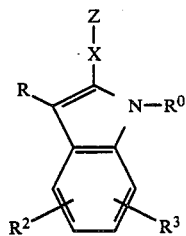

wherein: one of R and R$^0$ is

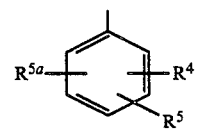

and the other is primary or secondary C$_{1-6}$ alkyl, C$_{3-6}$ cycloalkyl or phenyl—(CH$_2$)$_n$—;

X is —(CH$_2$)$_n$—or —CH=CH—;

n is 0, 1, 2 or 3;

Z is

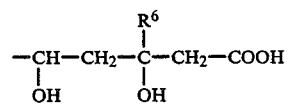

and

R$^4$, R$^5$, R$^{5a}$ and R$^6$ represent various substituents.

International patent application WO 84/02903 published Aug. 2, 1984 describes mevalonolactone analogs having the structures

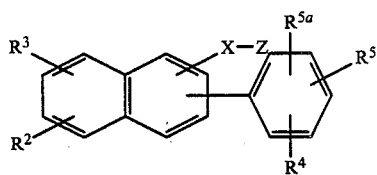

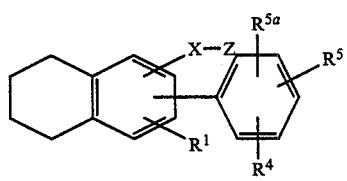

wherein X is —(CH$_2$)$_n$—,

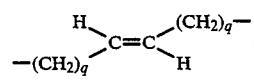

n=0, 1, 2, or 3 and both q's are 0 or one is 0 and the other is 1 and

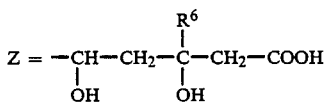

In *J. Med. Chem.*, 28, 347–358 (1985), G. E. Stokker, et al. report the preparation and testing of a series of 5-substituted 3,5-dihydroxypentanoic acids and their derivatives.

In *J. Med. Chem.*, 29, 159–169 (1986), W. F. Hoffman, et al. describe the preparation and testing of a series of 7-(substituted aryl)-3,5-dihydroxy-6-heptenoic (heptanoic) acids and their lactone derivatives. One of the preferred compounds in the reported series has the structure

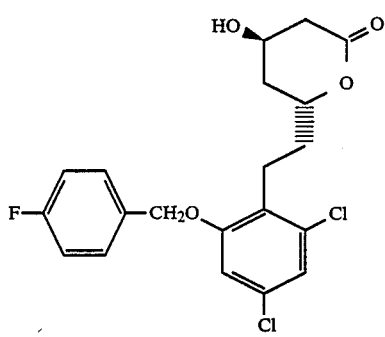

In *J. Med. Chem.*, 29, 170–181 (1986), G. E. Stokker, et al. report the synthesis of a series of 7-[3,5-disubstituted (1,1′-biphenyl)-2-yl]-3,5-dihydroxy-6-heptenoic acids and their lactones. Two of the preferred compounds reported in this article have the structures

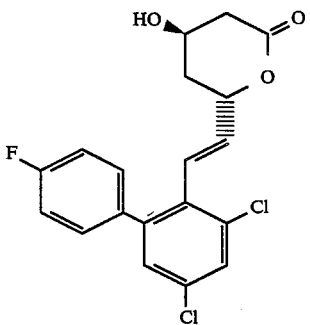

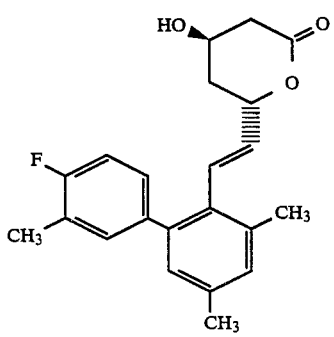

U.S. Pat. No. 4,613,610, issued Sept. 23, 1986 to J. R. Wareing describes pyrazole analogs of mevalonolactone and its derivatives useful for the treatment of hyperlipoproteinemia and atherosclerosis and having the general formula

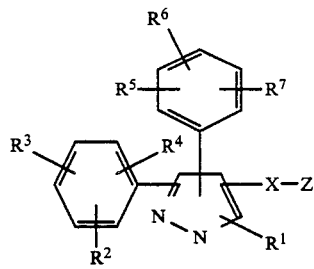

wherein X is $-(CH_2)_n-$, $-CH=CH-$, $-CH=CH-CH_2-$ or $-CH_2-CH=CH-$; n is 0, 1, 2 or 3, and $R^1$, $R^2$, $R^3$, $R^4$, $R^5$, $R^6$, $R^7$ and Z represent various substituents.

International patent application WO 86/07054 published Dec. 4, 1986 describes imidazole analogues of mevalonolactone having the general formula

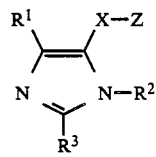

wherein $R^1$, $R^2$ and $R^3$ are $C_{1-6}$ alkyl not containing an asymmetric carbon atom, $C_{3-7}$ cycloalkyl, adamantyl-1 and $R^3$ may also be styryl or $R^1$, $R^2$ and $R^3$ are

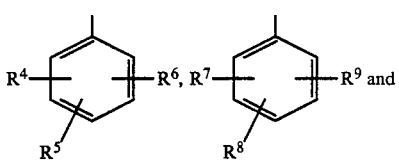

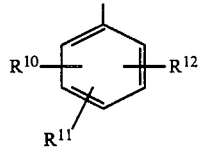

respectively, wherein $R^4$ to $R^{12}$ are various substituents; X is $-(CH_2)_m-$, $-CH=CH-$, $-CH=CH-CH_2$ or $-CH_2-CH=CH_2-$ wherein m is 0, 1, 2 or 3 and

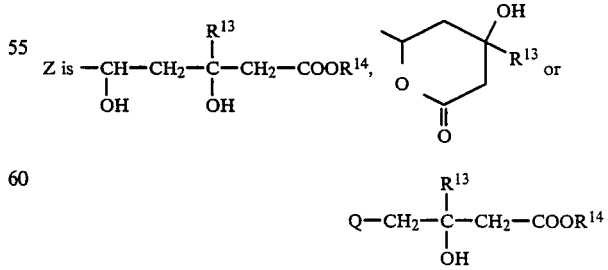

U.S. Pat. No. 4,681,893 issued July 21, 1987 to B. D. Roth describes certain pyrrol-1-yl compounds which are useful as hypocholesterolemic and hypolipidemic agents having the general formula

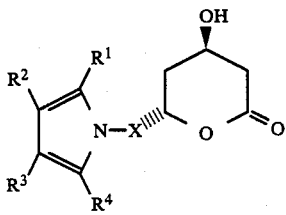

wherein X is —CH₂—, —CH₂CH₂—, —CH₂CH₂CH₂—, or CH₂CH(CH₃)—; and R¹, R², R³ and R⁴ represent various substituents.

U.S. Pat. No. 4,735,958 issued Apr. 5, 1988 to B. D. Roth et al describes certain pyrrol-1-yl compounds which are useful as hypocholesterolemic and hypolipidemic agents having the general formula

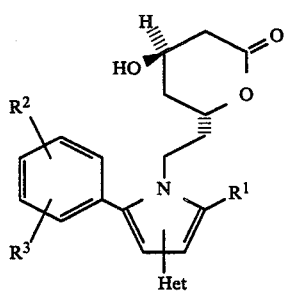

wherein R¹, R², R³ and Het represent various substituents.

SUMMARY OF THE INVENTION

This invention provides novel compounds having the formula

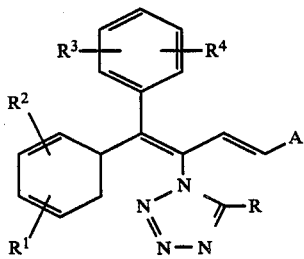

I wherein R, R¹, R², R³, and R⁴ are as defined below, which are potent inhibitors of the enzyme 3-hydroxy-3-methylglutaryl coenzyme A (HMG-CoA) reductase and are useful in the treatment of hypercholesterolemia, hyperlipoproteinemia and atherosclerosis. The present invention also provides useful intermediates, processes for their preparation and processes for the preparation of compounds of the Formula I.

DESCRIPTION OF THE INVENTION

The present invention provides novel tetrazol-1-yl compounds which are inhibitors of the enzyme HMG-CoA reductase, which are useful in the treatment of hypercholesterolemia, hyperlipoproteinemia and atherosclerosis, and which have the formula

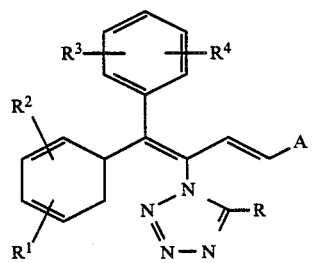

I wherein

R¹, R², R³ and R⁴ each are independently hydrogen, halogen, C₁₋₄ alkyl, C₁₋₄ alkoxy or trifluoromethyl;

R is hydrogen, C₁₋₄ alkyl or phenyl;

A

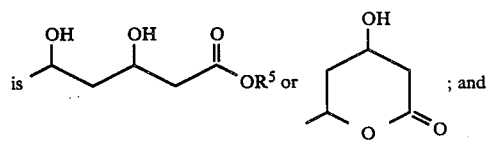

is                                                         ; and

R⁵ is hydrogen, a hydrolyzable ester group or a cation to form a non-toxic pharmaceutically acceptable salt.

This invention also provides processes for the preparation of the compounds of Formula I and to intermediates in the preparation of compounds of Formula I.

The terms "C₁₋₄ alkyl", "C₁₋₆ alkyl" and "C₁₋₄ alkoxy" as used herein and in the claims (unless the context indicates otherwise) mean unbranched or branched chain alkyl or alkoxy groups such as methyl, ethyl, propyl, isopropyl, butyl, isobutyl, t-butyl, amyl, hexyl, etc. Preferably, these groups contain from 1 to 4 carbon atoms and, most preferably, they contain 1 or 2 carbon atoms. Unless otherwise specified in the particular instance, the term "halogen" as used herein and in the claims is intended to include chlorine, fluorine, bromine and iodine while the term "halide" as used herein and in the claims is intended to include chloride, bromide and iodide anion. The term "a cation to form a non-toxic pharmaceutically acceptable salt" as used herein and in the claims is intended to include non-toxic alkali metal salts such as sodium, potassium, calcium and magnesium, the ammonium salt and salts with non-toxic amines such as trialkylamines, dibenzylamine, pyridine, N-methylmorpholine, N-methylpiperidine and other amines which have been used to form salts of carboxylic acids. Unless otherwise specified, the term "a hydrolyzable ester group" as used herein and in the claims is intended to include an ester group which is physiologically acceptable and hydrolyzable under physiological conditions such as C₁₋₆ alkyl, phenylmethyl and pivaloyloxymethyl.

In the compounds of Formula I, it is intended that all of the double bonds are in the trans configuration, i.e., (E), as indicated in the structural formulae used herein and in the claims.

As the compounds of the present invention may possess one or two asymmetric carbon atoms, the invention includes all of the possible enantiomeric and diastereomeric forms of the compounds of Formula I as described herein and in the claims. The compounds of Formula I which contain two centers of asymmetry may produce four possible stereoisomers designated as the RR, RS, SR and SS enantiomers; all four stereoisomers are considered within the scope of this invention. Specifically, the compounds of Formula I having two asymmetric carbon atoms bearing the hydroxy groups in the 3 and 5 position may produce four possible stereoisomers which are designated as the (3R,5S), (3S,5R), (3R,5R) and (3S,5S) stereoisomers. As used herein and in the claims, the term "(±)-erythro" is intended to include a mixture of (3R,5S) and (3S,5R) enantiomers, and the term "(±)-threo" is intended to include a mixture of (3R,5R) and (3S,5S) enantiomers. The use of a single designation such as (3R,5S) is intended to include mostly one stereoisomer. The lactone forms of the compounds of Formula I also have two asymmetric carbon atoms at the 4 and 6 position, and the resulting four stereoisomers may be designated as the (4R,6S), (4S,6R), (4R,6R) and (4S,6S) stereoisomers. As used herein and in the claims, the term "trans" lactone is intended to include a mixture of (4R,6S) and (4S,6R) enantiomers while the term "cis" lactone is intended to include a mixture of (4R,6R) and (4S,6S) enantiomers. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereoisomeric salts with optically active salt-forming agents, separating the mixture into diastereomeric salts and converting the separated salts into the free compounds. The possible enantiomeric forms may also be separated by fractionation through chiral high pressure liquid chromatography columns.

If it is desired to prepare the (+) isomer of the compounds of Formula I, then the synthetic (±) isomer of the present invention may be resolved by resolution methods well-known to those skilled in the art. For example of a resolution procedure in this general class of compounds, U.S. Pat. No. 4,375,475 issued Mar. 1, 1983 to A. K. Willard, et al. describe the resolution of a racemic (3S) trans lactone with excess d-(+)-α-methylbenzylamine (or the corresponding 1-(−)-α-methylbenzylamine), separating the resulting two diastereoisomeric amines and hydrolyizng to the corresponding, for example, sodium salt. The resulting salt may then be converted by conventional means to the corresponding acid, ester and lactone. Preferably, the optically active enantiomers of the compounds of Formula I may be prepared by stereoselective synthetic procedures, some of which are described herein. The use of optically active reagents in combination with the appropriate intermediate described herein would produce the desired enantiomer of the compound of Formula I.

Since the compounds of Formula I may contain varying amounts of solvent as ascertained mainly by elemental analysis, the present invention is intended to include solvates of the compounds of Formula I. In some cases, it appears that the products may be true solvates, while in other cases, the products may merely retain adventitious solvent or be a mixture of solvate plus some adventitious solvent. Preferably, the solvate is water and, most preferably, one to three moles of water. The examples below give the amount of solvent where appropriate in the analysis and melting points are those of the solvated product unless otherwise indicated.

In the compounds of Formula I, $R^1$, $R^2$, $R^3$, and $R^4$, independently, are preferably hydrogen, fluoro, chloro, methyl or methoxy, and most preferably, $R^1$ and $R^3$ are hydrogen and $R^2$ and $R^4$, independently, are hydrogen, fluoro, methyl or methoxy. It is preferred that R is hydrogen, methyl or phenyl and more preferably R is hydrogen or methyl. Preferably, $R^5$ is hydrogen, $C_{1-6}$ alkyl or a pharmaceutically acceptable cation. Most preferably, $R^5$ is a pharmaceutically acceptable cation especially sodium or potassium.

In the compounds of Formula I wherein A contains two asymmetric carbon atoms bearing the hydroxy group, the erythro isomer is preferred and the (3R,5S) isomer being most preferred. In the compounds of Formula I wherein A contains two asymmetric carbon atoms in the lactone form, the trans isomer is preferred and the (4R,6S) isomer being most preferred.

The compounds of Formula I may be prepared by various procedures, preferably starting from a compound of Formula II

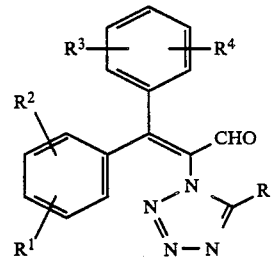

II wherein $R^1$, $R^2$, $R^3$ and $R^4$ each are independently hydrogen, halogen, $C_{1-4}$ alkyl, $C_{1-4}$ alkoxy or trifluoromethyl; and R is hydrogen, $C_{1-4}$ alkyl or phenyl.

The compounds of Formula IIa (compounds of Formula II wherein R is $C_{1-4}$ alkyl or phenyl) may be prepared from the optionally substituted benzophenones III by aldol condensation to the tetra substituted olefin V then hydrolysis to amide VI and conversion to the tetrazole ester VII followed by reduction of the ester group in compound VII with subsequent oxidation of the resulting alcohol VIII, as shown in Reaction Scheme 1.

Reaction Scheme 1

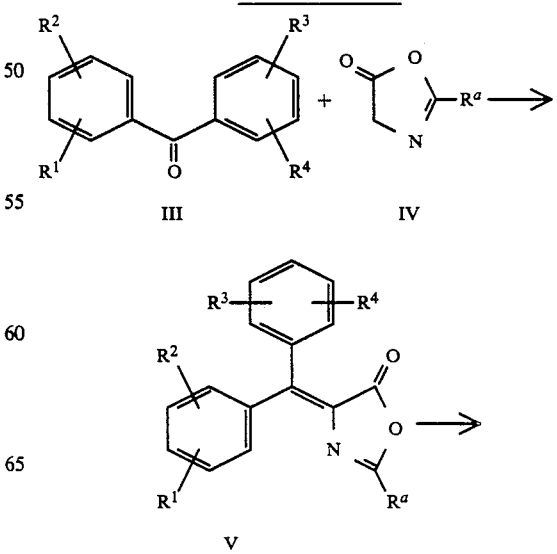

-continued
Reaction Scheme 1

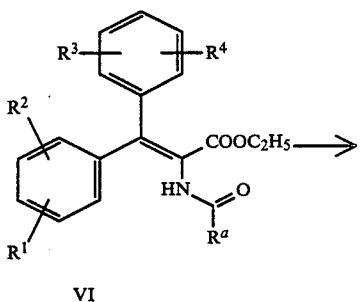

VI

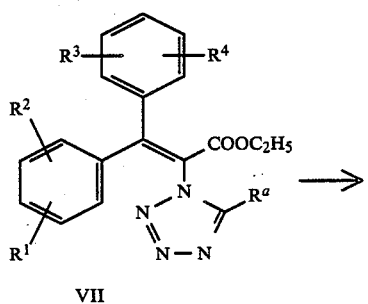

VII

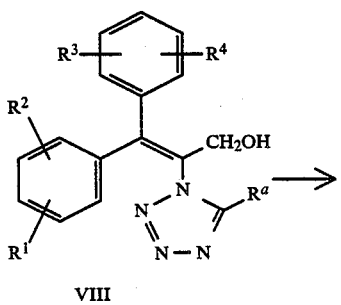

VIII

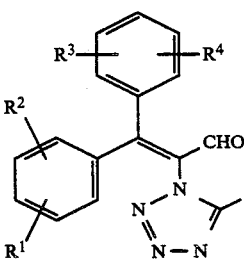

IIa

In Reaction Scheme 1, $R^a$ is $C_{1-4}$ alkyl or phenyl, $R^1$, $R^2$, $R^3$ and $R^4$ are as previously defined. The optionally substituted benzophenones of the Formula III may be prepared by the general and well-known Friedel Crafts reaction of a substituted phenyl catalyzed by Lewis acids, e.g., with aluminum chloride in carbon tetrachloride at about 0° C. A large number of substituted benzophenones are known and their prepartion are described in the art while many others are commercially available. For example, many of the starting materials of Formula III are described by G. Olah in *Friedel-Crafts and Related Reactions*, Vol. 3, Part 1 and 2, Interscience Publishers, New York, 1964 and references therein. The Friedel Crafts reaction may produce a mixture of benzophenones and, if so produced, the mixture may be separated by conventional techniques known in the art.

The appropriate benzophenone of the Formula III may be treated with the desired substituted azlactone of Formula IV which may be prepared by the general procedures described by A. K. Mukerjec in *Heterocycles*, 26(4), 1077 (1987). The reaction is conducted in an inert organic solvent such as tetrahydrofuran, carbon tetrachloride and mixtures thereof in the presence of titanium tetrachloride and a base, preferably pyridine, lutidine and the like until the production of the tetra substituted olefin V is essentially complete. The substituted oxazolones of Formula V may then be treated with a strong alkoxide base such as sodium alkoxide, potassium alkoxide and lithium alkoxide to produce the substituted amides of Formula VI. The amide group in compound VI is then converted to the heterocyclic tetrazol-1-yl moiety of compound VII by a two-step process. The amide is first treated with carbon tetrachloride in the presence of triphenylphosphine in a non-reactive solvent at about amibient temperature, then the mixture is treated with sodium azide and tetra n-butylammonium bromide.

The compounds of Formula IIb (compounds of Formula II wherein R is hydrogen) may be prepared from the optionally substituted benzophenones III by condensation with ethyl isocyanoacetate to the tetra substituted olefin IX and conversion to the tetrazol-1-yl ester XI through the isocyano intermediate X followed by reduction of the ester group in compound XI with subsequent oxidation of the resulting alcohol XII, as shown in Reaction Scheme 2.

Reaction Scheme 2

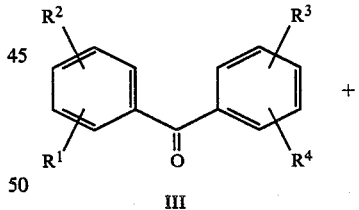

III

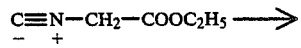

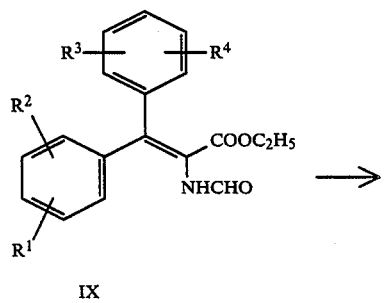

IX

-continued
Reaction Scheme 2

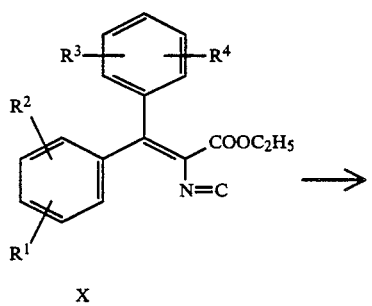

X

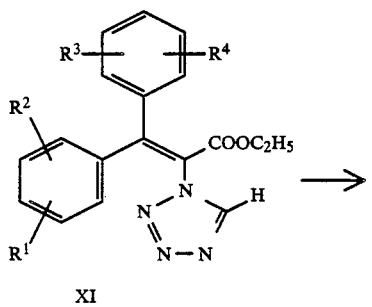

XI

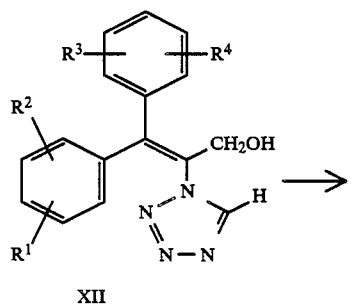

XII

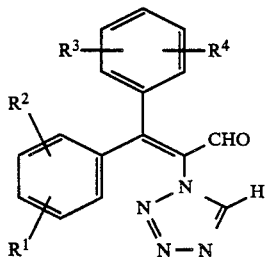

IIb

In Reaction Scheme 2, $R^1$, $R^2$, $R^3$ and $R^4$ are as previously defined. The appropriate benzophenone of the Formula III may be treated with ethyl isocyanoacetate in a non-reactive solvent preferably in tetrahydrofuran at about 0° C. in the presence of a strong base such as sodium hydride and lithium diisopropylamide. The formylamino olefin of Formula IX may then be treated in a non-reactive solvent and in the presence of a base such as triethylamine with phosgene which was dissolved in toluene. The resulting isocyano compound of Formula X is preferably treated in situ with sodium azide and tetra n-butylammonium bromide under reflux temperature of the solvent to produce the tetrazol-1-yl compound of Formula XI.

The tetrazole esters of the Formula VII (Reaction Scheme 1) and Formula XI (Reaction Scheme 2) may then be converted by standard techniques to the alcohols VIII and XII, respectively, by a series of known reactions. According to one reaction route, the compound of Formula XI is first hydrolyzed by conventional methods, such as base hydrolysis, i.e., lithium hydroxide, potassium hydroxide and sodium hydroxide. The resulting acid (i.e. Example 23) is then converted to an acyl chloride by reacting with a reagent such as oxalyl chloride in methylene chloride at reflux temperature and the resulting acyl chloride is reduced with a reducing agent, preferably, lithium aluminum hydride in tetrahydrofuran at $-78°$ C. to produce the alcohol of the Formula XII. The alcohol of Formula VIII may be prepared from the ester of Formula VII by a similar series of reactions utilized to convert the ester XI to the alcohol XII. Alternatively, and more preferably, the alcohols VIII and XII may be prepared in one step from the corresponding esters VII and XI by reduction with reducing agents such as diisobutylaluminum hydride in a non-reducible inert solvent such as methylene chloride, at low temperatures, preferably at about $-78°$ C.

The allylic alcohols of Formulae VIII and XII may be readily oxidized by conventional oxidizing agents such as pyridinium chlorochromate in a non-reactive solvent, preferably, methylene chloride at ambient temperature to produce the corresponding allylic aldehydes of Formula IIa and IIb.

The compounds of Formula I may be prepared from a novel aldehyde of the Formula II wherein $R^6$ is a hydrolyzable ester group and R, $R^1$, $R^2$, $R^3$ and $R^4$ are as previously defined by the general reaction route shown in Reaction Scheme 3.

Reaction Scheme 3

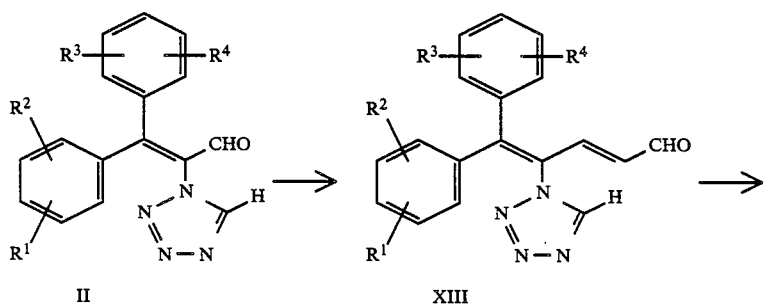

-continued
Reaction Scheme 3

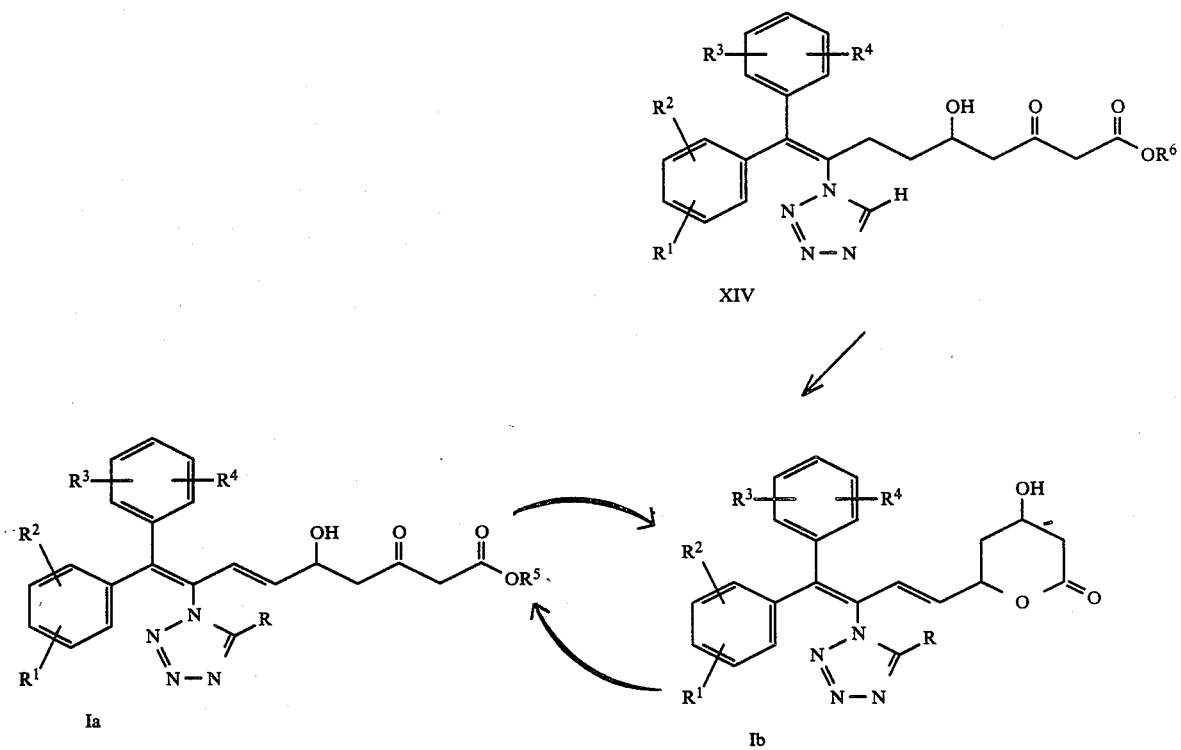

In Reaction Scheme 3, an allylic aldehyde of Formula II may be treated with triphenylphosphoranylidene acetaldehyde in a non-reactive solvent such as benzene, toluene, tetrahydrofuran, 1,2-dimethoxyethane and the like. The temperature of the reaction is not critical and can be conducted at from ambient temperature to the reflux temperature of the solvent. For convenience we prefer to conduct the reaction at reflux temperature. It should be understood and appreciated by those skilled in the art that the reaction conditions and the number of equivalents of triphenylphosphoranylidene acetaldehyde utilized per equivalent of a compound of Formula IIa is critical. Preferably, the reaction is conducted with about one equivalent of Witting reagent under controlled reaction conditions.

The penultimate intermediate of Formula XIV wherein $R^6$ is a hydrolyzable ester group such as methyl, ethyl and t-butyl ester may be prepared from the corresponding aldehyde of Formula XIII by reaction with the dianion of acetoacetate ester generated in situ, for example, as described in Example 8. The reaction may be conducted in an inert organic solvent such as tetrahydrofuran at low temperatures from −78° C. to about 0° C. and preferably from about −78° C. to −40° C. until the reaction is essentially complete. The ketone ester of Formula XIV may be reduced to the dihydroxy ester of Formula Ia by reduction of the ketone radical with reducing agents well-known in the art, e.g., sodium borohydride, sodium cyanoborohydride, zinc borohydride, disiamylborane, diborane, ammonia borane, t-butylamine borane, pyridine borane, lithium tri-s-butylborohydride or other similar reducing agents which will not reduce nor hydrolyze the carboxylic ester radical. Preferably, the reduction is carried out in a stereospecific manner by a two-step stereospecific reduction in order to maximize the production of the preferred erythro isomer of the compound of Formula I. The stereospecific reduction of a compound of Formula XIV is carried out with trisubstitutedalkylboranes, preferably triethylborane, or alkoxydialkylboranes, preferably methoxydiethylborane or ethoxydiethylborane [*Tetrahedron Letters*, 28, 155 (1987)] at a temperature of about −70° C. to about ambient temperature. The complex which is produced is then reduced with sodium borohydride at a temperature of about −50° C. to about −78° C. in an inert organic solvent such as tetrahydrofuran, diethyl ether and 1,2-dimethoxyethane, preferably, tetrahydrofuran. The reduction is then completed by the addition of methanol. The resulting compound of Formula Ia produced from the stereospecific reduction contains two asymmetric carbon atoms bearing the hydroxy group in an erythro configuration. Thus, reduction of the ketone radical under the conditions employed herein produces mostly the erythro isomers of the compounds of Formula Ia and only a small amount of the less preferred threo isomers. The ratio of erythro-threo isomers produced will vary according to the specific compound utilized and the reaction conditions employed. Normally, this ratio will be approximately 9:1 to 9.8 : 0.2. However, the use of a non-specific reduction will normally produce a 1:1 mixture of isomers. Nevertheless, the mixture of isomers may be separated and purified by conventional techniques and then converted to the compounds of general Formula I in a conventional manner well-known to those skilled in the art.

The preparation of a compound of Formula Ia wherein $R^5$ is a cation is preferably carried out by base hydrolysis of a compound of Formula Ia wherein $R^5$ is a hydrolyzalable ester group with bases such as sodium hydroxide, potassium hydroxide and lithium hydroxide in an organic solvent such as tetrahydrofuran, ethanol and methanol at a temperature from 0° C. to about 50° C. The form of the cation is normally determined by the corresponding cation of the hydroxide employed. However, if desired, the cation may be exchanged for another cation by treatment with ion-exchange resins.

The compound of Formula Ia may be cyclized to the corresponding lactone of Formula Ib by conventional lactonization methods, for example, by heating the acid in an inert organic solvent such as benzene, toluene and xylene and azetropically removing the water which is produced or by treating the compound of Formula Ia in an inert organic solvent, e.g., toluene, benzene, diethyl ether or methylene chloride with an acid such as p-toluenesulfonic acid, in the presence of a drying agent, e.g., NaSO$_4$, MgSO$_4$ or molecular sieves. Preferably, the lactonization may be carried out by activation of the carboxyl radical with a carbodiimide in an inert organic solvent such as tetrahydrofuran, and preferably, in methylene chloride or ethyl acetate at about ambient temperature to produce the lactone of Formula Ib. If the relative stereochemical configuration of the two carbon atoms bearing the hydroxy groups are established as erythro in Formula Ia, then the lactonization will produce the preferred trans lactone of Formula Ib, otherwise the lactonization will produce a mixture of trans and cis lactones. The resulting lactone of Formula Ib may, if desired, be hydrolyzed with base or acid to produce the compounds of Formula Ia.

In an alternate reaction route, the preparation of compounds of Formula I may be prepared from intermediates of Formula XVI, as shown in Reaction Scheme 4.

Reaction Scheme 4

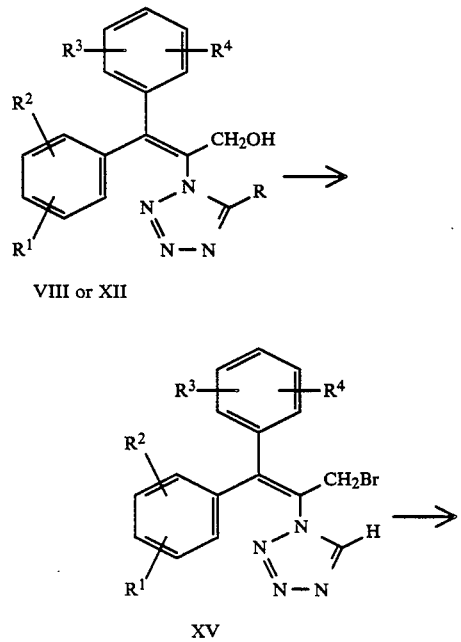

VIII or XII

XV

-continued
Reaction Scheme 4

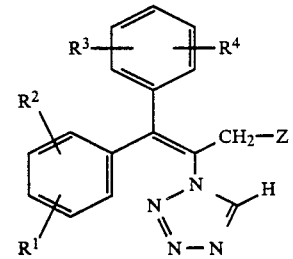

XVI

In Reaction Scheme 4, R, $R^1$, $R^2$, $R^3$ and $R^4$ are as previously defined and Z is

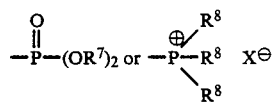

in which $R^7$ is $C_{1-4}$ alkyl, $R^8$ is phenyl which is unsubstituted or substituted by one or two $C_{1-4}$ alkyl or chloro substituents and X is bromo, chloro or iodo. The allylic bromide of Formula XV may be prepared from the alcohols of Formula VIII or XII by treatment with carbon tetrabromide and triphenylphosphine.

The allylic bromide of Formula XV may be reacted in a conventional manner with phosphines such as triphenylphosphine in an inert organic solvent such as cyclohexane to produce the phosphonium salt of Formula XVI. Alternatively, the allylic bromide of Formula XV may be reacted in a conventional manner with phosphites such as trimethyl phosphite and triethyl phosphite either neat or in an inert organic solvent, and preferably, neat to produce the phosphonates of Formula XVI.

The compounds of Formula I may be prepared from an intermediate of Formula XVI by the reaction with aldehyde intermediates well known to those skilled in the art. The phosphonium salt or phosphonate of Formula XVI may be reacted with silyl protected aldehydes in a similar manner as described in *Tetrahedron Letters*, 25, 2435 (1984) and U.S. Pat. No. 4,571,428 to produce erythro compounds of Formula Ia. A compound of Formula XVI may also be reacted with optically active aldehydes as described in *Tetrahedron Letters*, 23, 4305 (1982) and U.S. Pat. No. 4,613,610 to produce the (4R,6S) enantiomer of a compound of Formula Ib which can, if desired, be converted to the (3R, 5S) enantiomer of a compound of Formula Ia. The methods described above as well as other methods are described in U.S. patent application Ser. No. 151,513 filed Feb. 18, 1988 by us.

When it is desired to prepare mostly one stereoisomer of a compound of Formula I, it is preferred to employ optically pure starting materials. The various procedures which may be used to prepare one isomer of a compound of Formula I is illustrated in Reaction Schemes 5 and 6. The most preferred isomer of a compound of Formula I wherein A is defined as

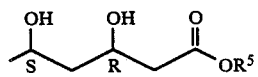

is the (3R, 5S) isomer, and the most preferred isomer of a compound of Formula I wherein A is defined as

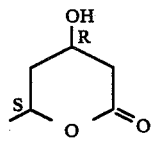

is the (4R, 6S) isomer. It should be appreciated that it is necessary to have only one of the above definitions of A for compounds of Formula I since they may be interconverted as shown in Reaction Scheme 3. To illustrate the use of optically pure starting materials, the preparation of a preferred embodiment of compounds of Formula I such as the (3R, 5S) isomer of compounds of Formula Ia and the (4R, 6S) isomer of compounds of Formula Ib is shown in Reaction Scheme 6.

Another particularly preferred method envisioned for the preparation of compounds of the Formula Ia and Ib of the present invention is the use of intermediates having the formulae

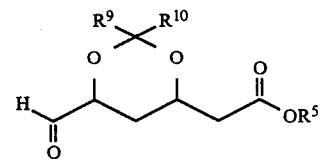 XVIIa

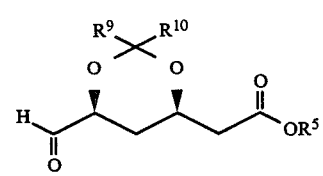 XVIIb in substantially the cis form wherein $R^9$ and $R^{10}$ each are $C_{1-4}$ alkyl or $R^9$ and $R^{10}$, taken together with the carbon atom to which they are attached, is cyclopentyl, cyclohexyl or cycloheptyl and $R^{10}$ is hydrogen, $C_{1-4}$ alkyl or a metal cation. The preparation and use of the compounds of Formulae XVIIa and XVIIb is described herein and in William T. Han and John J. Wright U.S. patent application Ser. No. 156,865, filed Feb. 18, 1988. The use of the intermediates of Formula XVIIa and Formula XVIIb is shown in Reaction Schemes 5 and 6, respectively.

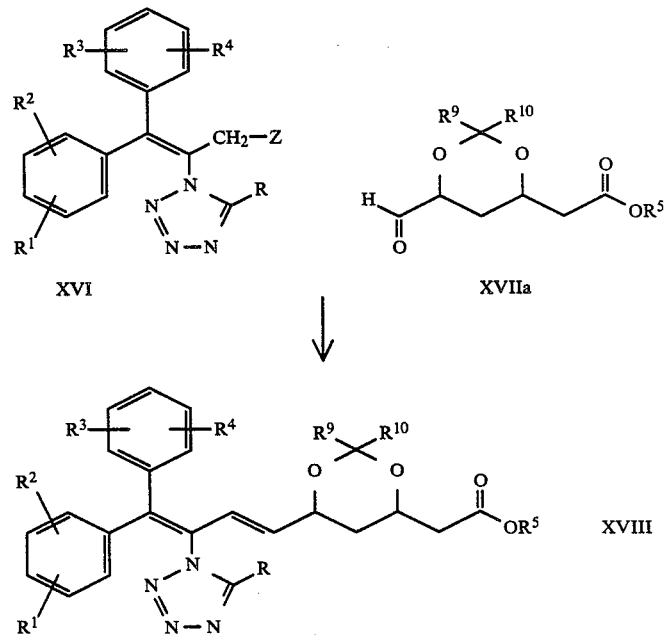

Reaction Scheme 5

Reaction Scheme 5
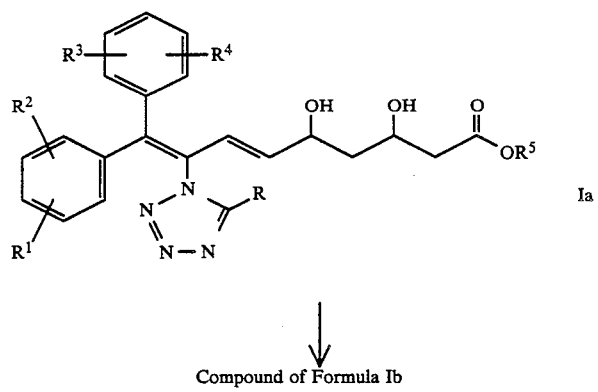
Compound of Formula Ib
Reaction Scheme 6
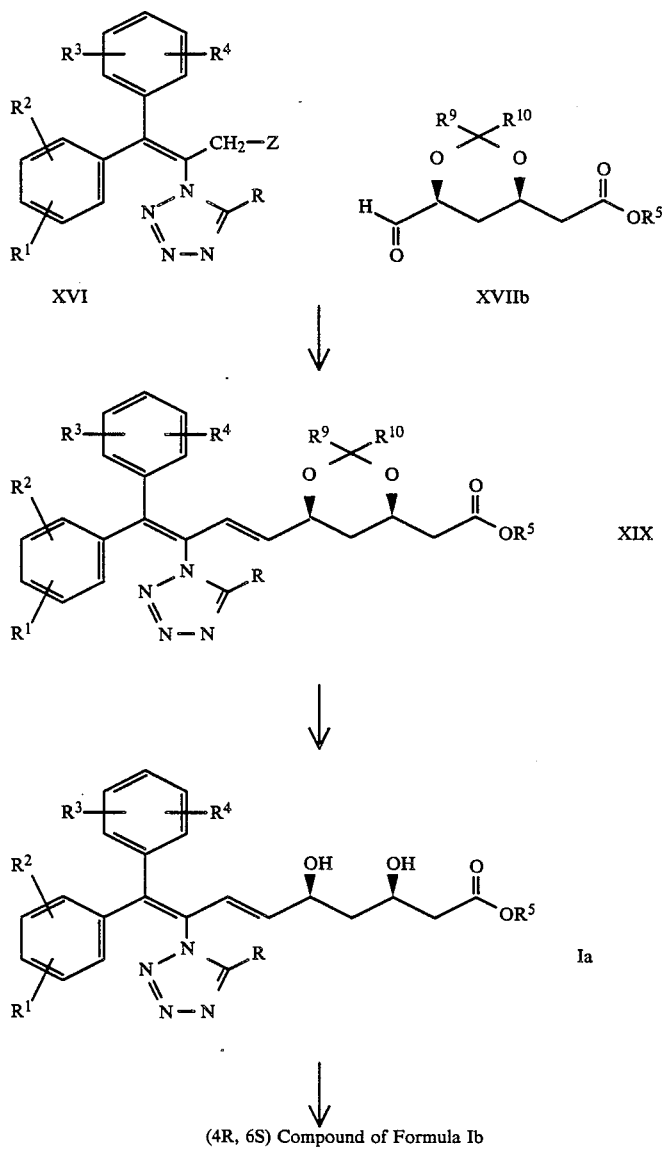
(4R, 6S) Compound of Formula Ib
In Reaction Schemes 5 and 6, R, $R^1$, $R^2$, $R^3$, $R^4$ and $R^5$, are as previously defined;

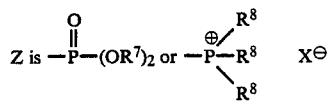

in which $R^7$ is $C_{1-4}$ alkyl, $R^8$ is phenyl which is unsubstituted or substituted by one or two $C_{1-4}$ alkyl or chloro substituents; X is bromo, chloro or iodo and $R^9$ and $R^{10}$ each are independently hydrogen, $C_{1-6}$ alkyl or phenyl which is optionally substituted by one or two $C_{1-4}$ alkyl, halogen, $C_{1-4}$ alkoxy or trifluoromethyl. The preparation of the phosphonium salt and the phosphonate of Formula XVI is shown in Scheme 4. The reaction of a compound of Formula XVI with a compound of Formula XVIIa or Formula XVIIb to produce a compound of Formula XVIII or XIX, respectively, wherein $R^5$ is $C_{1-4}$ alkyl may be carried out in an inert organic solvent such as tetrahydrofuran and N,N-dimethylformamide in the presence of a strong base such as n-butyllithium at a temperature of about $-50°$ C. to about $-78°$ C. When the reaction of a compound of Formula XVI is carried out with a compound of Formula XVIIa or XVIIb wherein $R^5$ is hydrogen, it is preferred to use two equivalents of a strong base such as n-butyllithium. Alternatively, the salt of a compound of Formula XVIIa or XVIIb may be prepared which is then treated with a compound of Formula XVI and a strong base. The methods of addition, salt formation and ylide preparation are well-known to those skilled in the art. The tetrazol-1-yl compounds of Formula XVIII or XIX may be readily deprotected by well-known procedures such as mild acid, e.g., 0.2N HCl and 0.5N HCl in an inert organic solvent such as tetrahydrofuran to produce the erythro compounds of Formula Ia or the (3R, 5S) compounds of Formula Ia which may then be converted to the trans compounds of Formula Ib or (4R, 6S) compounds of Formula Ib in a conventional manner well-known to those skilled in the art.

In a preferred embodiment of the invention the compounds of Formula I have the structure

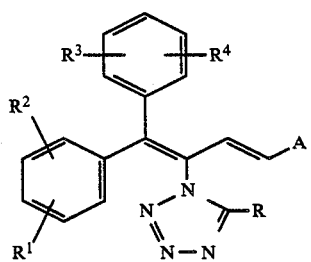

wherein
$R^1$, $R^2$, $R^3$ and $R^4$ each are independently hydrogen, fluoro, chloro, methyl or methoxy;
R is hydrogen, $C_{1-4}$ alkyl or phenyl;
A is

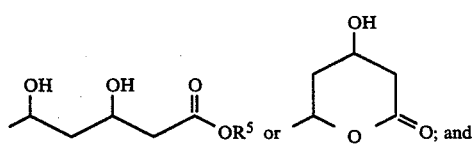

$R^5$ is hydrogen, a hydrolyzable ester group or a cation to form a non-toxic pharmaceutically acceptable salt.

In a more preferred embodiment of the invention the compounds of Formula I have the structure

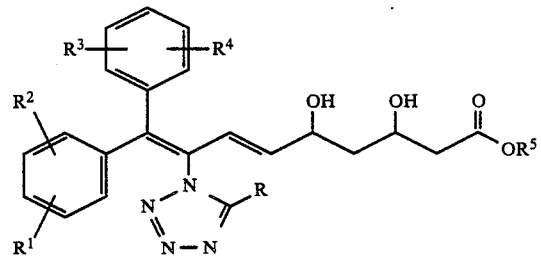

wherein $R^1$, $R^2$, $R^3$, and $R^4$ each are independently hydrogen, fluoro, chloro, or methyl; R is hydrogen, methyl or phenyl; and $R^5$ is hydrogen, $C_{1-6}$ alkyl or a cation to form a non-toxic pharmaceutically acceptable salt. In a particularly preferred embodiment, R is hydrogen.

In another more preferred embodiment of the invention the compounds of Formula I have the structure

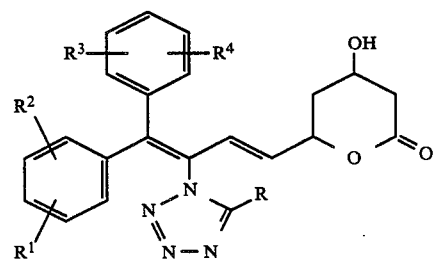

wherein $R^1$, $R^2$, $R^3$, and $R^4$ each are independently hydrogen, fluoro, chloro, or methyl; and R is hydrogen, methyl or phenyl. In a particularly preferred embodiment, R is hydrogen.

In another aspect, this invention provides novel intermediates of the formula

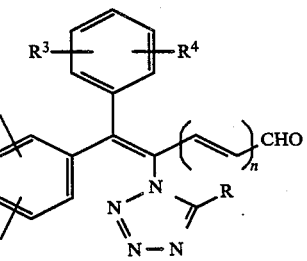

XXX wherein $R^1$, $R^2$, $R^3$ and $R^4$ each are independently hydrogen, halogen, $C_{1-4}$ alkyl, $C_{1-4}$ alkoxy, or trifluoromethyl; n is zero or 1; and R is hydrogen, $C_{1-4}$ alkyl or phenyl.

In a preferred embodiment, the compounds of Formula XXX have the structure

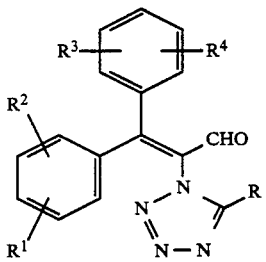

wherein $R^1$, $R^2$, $R^3$ and $R^4$ each are independently hydrogen, fluoro, chloro, or methyl; and R is hydrogen, methyl or phenyl.

In another preferred embodiment, the compounds of Formula XXX have the structure

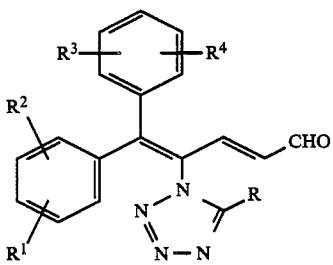

wherein $R^1$, $R^2$, $R^3$ and $R^4$ each are independently hydrogen, fluoro, chloro or methyl; and R is hydrogen, methyl or phenyl.

In still another aspect, this invention provides novel intermediates of the formula

XIV

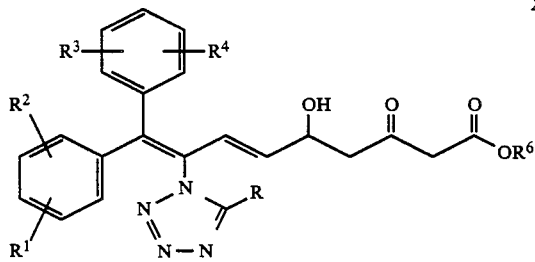

wherein $R^1$, $R^2$, $R^3$ and $R^4$ each are independently hydrogen, halogen, $C_{1-4}$ alkyl, $C_{1-4}$ alkoxy or trifluoromethyl; R is hydrogen, $C_{1-4}$ alkyl or phenyl; and $R^6$ is a hydrolyzable ester group.

The compounds of Formula I are competitive inhibitors of the enzyme 3-hydroxy-3-methylglutaryl coenzyme A (HMG-CoA) reductase, the rate limiting enzyme in cholesterol biosynthesis, and therefore, are selective suppressors of cholesterol biosynthesis in animals, including man. Consequently, they are useful in the treatment of hypercholesterolemia, hyperlipoproteinemia and atherosclerosis. The biological activity of the compounds of Formula I may be demonstrated in the following biological tests.

Test A: In Vitro Inhibition of Microsomal HMG-CoA Reductase:

The intact, fully activated microsomal form of rat liver HMG-CoA reductase (subunit MW ca 100,000 daltons) was prepared as described by Parker, et al., Biochem. Biophys. Res. Commun., 125, 629-635 (1984), and used as the source of enzyme for assays. HMG-CoA reductase activity was determined essentially by the method of Shapiro, et al., Biochem. Biophys. Acta., 370, 369-377 (1974), with modifications as described by Ingebritsen and Gibson, Meth. Enzymol. 71, 486-497 (1981) with the exception that the internal standard $^3$H-mevalonolactone is added after termination of the assay. In this procedure, the enzyme is assayed by measuring the formation of product, $^{14}$C-mevalonate, from the substrate, [3-$^{14}$C]-HMG-CoA, in the presence of NADPH. The $^{14}$C-mevalonate is converted to its lactone and isolated by silica thin-layer chromatography (Whatman LK5D, developed in 50:50 benzene:acetone) in the presence of $^3$H-mevalonolactone as an internal standard. Assays were conducted under conditions in which product formation was linear with respect to time and enzyme concentration.

To measure reductase inhibition, test compounds dissolved in water or dimethylsulfoxide and diluted in buffer A (50 mM imidazole-HCl, 250 mM NaCl, 1 mM EDTA, 1 mM EGTA, 5 mM DTT, 20 μM leupeptin, pH=7.2) were incubated with aliquots of microsomes (80–160 μg protein in buffer A) followed by addition of d,1-[3-$^{14}$C]-HMG-CoA (0.33 mM, 2.0 dpm/picomole) and NADPH (3.0 mM). The 50 percent inhibitory concentration ($IC_{50}$) for each compound in Table 1 was calculated from the linear regression line of the percent decrease (from control) in enzyme activity vs. log concentration of inhibitor, determined using at least 4 dilutions of each test compound assayed in duplicate.

TABLE 1

| Inhibition of Microsomal HMG-CoA Reductase | |
|---|---|
| Compound of Example No. | $IC_{50}$ μmolar |
| 20 | 0.75 |
| 28 | 0.12 |

Test B: Isolated Hepatocyte Cholesterol Biosynthesis Assay:

Intact parenchymal hepatocytes were isolated from male Wistar rats (180–280 g) fed cholestyramine containing or normal diet, using the collagenase perfusion method essentially as described by Seglen, in Methods in Cell Biology (D. Prescott, ed.) Vol. 13, pp. 29–83, Academic Press, New York (1976). Cell preparations were used only when viability (trypan blue exclusion) exceeded 90%. Cholesterol biosynthesis was determined as the incorporation by hepatocytes of $^3$H from [$^3$H]-water into total (cellular plus medium) 3β-hydroxy sterols as per Ingebritsen, et al., J. Biol. Chem., 254, 9986–9989 (1979). Hepatocyte sterols and lipids were isolated by a modification of the methods described by Kates, in Techniques in Lipidology, (M. Kates, ed.), pp. 349, 360–363, North Holland Publ. Co., Amsterdam, 1972. To isolate sterols, cells are extracted with methanol:chloroform:water (2:1:0.8), the chloroform phase is separated and extracted with benzene to remove traces of water, then dried under nitrogen. The residue is saponified at 75° C. with 0.30N NaOH in methanol:water (9:1). The alkaline mixture is then extracted three times with petroleum ether to yield the non-saponifiable lipids which include the free as well as initially esterified cholesterol. The extract is dried under nitrogen in the presence of carrier cholesterol (0.1 mg) and 10% benzene, and the residue is dissolved in acetone:ethanol (1:1). Finally, the 3β-hydroxysterols are precipitated with an excess of digitonin, the precipitate is washed in acetone, dried under nitrogen, and dissolved in toluene:methanol (1:1). The $^3$H-labelled sterols are quantified by liquid scintillation and corrected for counting efficiency. In some tests $^{14}$C-cholesterol was added to initial extractions as an index of recovery, which averaged 80±3%.

To measure inhibition of cholesterol synthesis, duplicate or triplicate aliquots of freshly isolated cells were suspended (100 mg cell net weight in 2.0 mL) in Eagle's Minimal Essential Medium containing bicarbonate and HEPES buffer, pH 7.35, plus 2% bovine serum albumin under a 95% $O_2$+5% $CO_2$ atmosphere. Cells were preincubated for 10 minutes with or without aliquots of test compounds added as water solutions of sodium salts or as dimethylsulfoxide solutions of lactones. Controls received vehicle alone. [$^3$H]-water (1.0 mCi per mL incubation volume) or 2-$^{14}$C-acetate (0.5 μCi per mL incubation volume) was then added to each and the cells were incubated with constant shaking for 60 minutes at 37°. These conditions produced time-linear incorporation of tritium or $^{14}$C into sterols. The $IC_{50}$ for inhibition of sterol synthesis by test compounds which is shown in Table 2 was calculated from the linear regression curve of % inhibition (compared to controls) vs. log concentration using at least 4 concentrations of inhibitor. Test B therefore measures the ability of test substances to inhibit the intracellular synthesis of cholesterol.

TABLE 2

| Inhibition of Isolated Hepatocyte Cholesterol Biosynthesis | |
|---|---|
| Compound of Example No. | $IC_{50}$ nmolar |
| 20 | 100 |
| 28 | 20.0 |
| Mevinolin (Lovastatin) | 46.0 ± 26 |

The results of the above Tests A and B demonstrate that the compounds of Formula I inhibit cholesterol biosynthesis and, therefore, are useful in the treatment of hypercholesterolemia.

In another embodiment, this invention includes pharmaceutical compositions comprising at least one compound of Formula I in combination with a pharmaceutical carrier or diluent.

In another embodiment, this invention relates to a method of inhibiting cholesterol biosynthesis in an animal in need thereof, which comprises administering to said animal an effective cholesterol inhibitory dose of at least one compound of Formula I.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or nonaqueous liquid suspension, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active component, that is, the compound of Formula I according to the invention.

The compounds of Formula I may also be co-administered with pharmaceutically acceptable non-toxic cationic polymers capable of binding bile acids in a non-reabsorbable form in the gastrointestinal tract, e.g., cholestyramine, colestipol and poly [methyl-(3-trimethyl-aminopropyl)iminotrimethylene dihalide]. The relative amounts of polymer to compounds of this invention is between about 10:1 to about 10,000:1.

The dosage of the compounds of Formula I will depend not only on such factors as the weight of the patient and mode of administration, but also on the degree of cholesterol biosynthesis inhibition desired and the potency of the particular compound being utilized. The decision as to the particular dosage to be employed (and the number of times to be administered per day) is within the discretion of the physician, and may be varied by titration of the dosage to the particular circumstances of this invention for the satisfactory inhibition or reduction of cholesterol biosynthesis, each oral dosage unit will contain the active ingredient in an amount of from about 0.01 mg/kg to about 10 mg/kg body weight, and most preferably from about 0.05 mg/kg to about 2 mg/kg body weight. The active ingredient will preferably be administered in equal doses from one to four times a day. However, usually a small dosage is administered, and the dosage is gradually increased until the optimal dosage for the host under treatment is determined.

DESCRIPTION OF SPECIFIC EMBODIMENTS

In the following examples, all temperatures are given in degrees Centigrade. Melting points were recorded on a Haake-Buchler Melting Point Apparatus and are uncorrected. Proton magnetic resonance ($^1$H NMR) spectra were recorded on a Bruker AM 300, Burker WM 360, Varian or Varian Gemini 300 Spectrometer. All spectra were determined in $CDCl_3$, DMSO-$d_6$ or $D_2O$ unless otherwise indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; dt, doublet of triplet; and dq, doublet of quartet. Carbon-13 nuclear magnetic resonance ($^{13}C$ NMR) spectra were recorded on a Bruker AM 300 or Varian VXL 200 spectrometer and were broad band proton decoupled. All spectra were determined in $CDCl_3$, $DMSO-d_6$ or $D_2O$ unless otherwise indicated with internal deuterium lock and chemical shifts are reported in $\delta$ units downfield from tetramethylsilane. Infrared (IR) spectra were determined on a Nicolet MX-1 FT spectrometer from 4000 $cm^{-1}$ to 400 $cm^{-1}$, calibrated to 1601 $cm^{-1}$ absorption of a polystrene film and are reported in reciprocal centimeters ($cm^{-1}$). Relative intensities are indicated as follows: s (strong), m (medium) and w (weak).

Mass spectra were recorded on a Kratos MS-25 instrument utilizing the fast atom bombardment (FAB) technique. The mass data are expressed in the format: parent ion ($M^+$) or protonated ion $(M+H)^+$.

Analytical thin-layer chromatography (TLC) was carried out on precoated silica gel plates (60F-254) and visualized using UV light, iodine vapors and/or staining with one of the following reagents: (a) methanolic phosphomolybdic acid (2%) and heating; (b) reagent (a) followed by 2% cobalt sulphate in 5M $H_2SO_4$ and heating. Column chromatography, also referred to as flash column chromatography, was performed in a glass column using finely divided silica gel (32–63 μm on silica gel-H) and pressures somewhat above atmospheric pressure with the indicated solvents. All evaporations of solvents were performed under reduced pressure. As used herein, the term hexanes is a mixture of isomeric $C_6$ hydrocarbons as specified by the American Chemical Society, and the term "inert" atmosphere is an argon or nitrogen atmosphere unless otherwise indicated.

Example 1

2-Phenyl-5-oxo-4,5-dihydro-1,3-oxazole

The title azlactone was prepared according to the general procedure described by A. K. Mukerjec, *Heterocycles*, 26(4), 1077, (1987), and the product was purified by crystallization from hexanes.

Example 2

4-[Bis(4-fluorophenyl)methylene]-3-phenyl-5-(4H-oxazolone)

To a 2-liter round-bottom flask containing 410 mL of dry tetrahydrofuran at 0° C. was added a solution of titanium tetrachloride (85 mL) in carbon tetrachloride (170 mL) over a period of 45 minutes. To this stirred pale yellow suspension was added dropwise a mixture containing 34 g of 4,4-difluorobenzophenone, 25 g of 2-phenyl-5-oxo-4,5-dihydro-1,3-oxazole in 115 mL of dry tetrahydrofuran and 60 mL of pyridine. The addition took 30 minutes to complete and the thick, greenish suspension was stirred at 0° C. for 2 hours, then at 35° C. for 4 hours. The dark brownish suspension (somewhat thinner than before) was quenched by slow addition of 1 liter of water. The organic phase was separated and washed twice with water. The organic layer was dried ($MgSO_4$), decolorized (activated charcoal) and evaporated to give a semi-solid. The crude product was recrystallized from hexanes to give 45.5 g (80.8%) of the title compound as large, yellowish needles; m.p.=141°–143° C.

Anal. Calcd. for $C_{22}H_{13}F_2NO_2$: C, 73.13; H, 3.63; H, 3.88; Found: C, 73.02; H, 3.60; H, 3.88.

Example 3

Ethyl 3,3-bis(4-fluorophenyl)-2-benzoylamino-2-propenoate

A solution of sodium ethoxide in ethanol was prepared by dissolving 0.4 g of sodium metal in 150 mL of absolute ethanol. To this solution was added 5.3 g of 4-[bis(4-fluorophenyl)methylene]-3-phenyl-5-(4H-oxazolone) and the resulting clear solution was stirred at room temperature for one hour. The reaction mixture was neutralized with 4 mL of glacial acetic acid and filtered to remove sodium acetate. The product was crystallized from hexanes-ethyl acetate mixture to yield 5.8 g (97%) of the title compound; m.p.=171.3°–172.1° C.

Anal. Calcd. for $C_{24}H_{19}F_2NO_3$: C, 70.75; H, 4.70; N, 3.43; Found: C, 70.64; H, 4.69; N, 3.39.

Example 4

Ethyl 3,3-bis(4-fluorophenyl)-2-(5-phenyl-1H-tetrazol-1-yl)-2-propenoate

To a suspension of 5.8 g (14 mmoles) of ethyl 3,3-bis-(4-fluorophenyl)-2-(benzoylamino)-2-propenoate and 11.2 g of triphenylphosphine in 150 mL of dry acetonitrile at room temperature was added dropwise 8.3 mL of carbon tetrachloride. The pale suspension was stirred for 45 minutes. To this clear orange solution was added 2.8 g of sodium azide and 1 g of tetra n-butyl ammonium bromide and stirring was continued. The orange suspension soon became pale with the formation of a white precipitate. After three hours, the mixture was filtered and the solution was concentrated under reduced pressure. More triphenylphosphine oxide was removed and the desired product was purified by crystallizations from ethyl acetate-hexanes to give 4.2 g (69%) of the title compound; m.p.=148.6–150.1° C.

Anal. Calcd. for $C_{24}H_{18}F_2N_4O_2$: C, 66.66; H, 4.20; N, 12.96; Found: C, 65.91; H, 4.26; N, 12.82.

Example 5

3,3-Bis(4-fluorophenyl)-2-(5-phenyl-1H-tetrazol-1-yl)-2-propenol

To a solution of 3.5 g (8.2 mmoles) of ethyl 3,3-bis-(4-fluorophenyl)-2-(5-phenyl-1H-tetrazol-1-yl)-2-propenoate in 75 mL of dry methylene chloride at −80° C. under argon was added dropwise 18 mL (1.0M, 18 mmoles) of diisobutylaluminum hydride in methylene chloride. The clear solution was stirred at −80° C. for 10 minutes then monitored by TLC. An additional 5 mL of diisobutylaluminum hydride in methylene chloride was added to the mixture and stirring was continued for 30 minutes. The reaction mixture was quenched with 2M HCl and the product was extracted into ethyl acetate. The organic layers were combined, dried over $MgSO_4$ and evaporated to a semi-solid. Recrystallization from ethyl acetate-hexanes mixture gave 3.2 g (99%) of the title compound; m.p.=196.6°–197.6° C.

Anal. Calcd. for $C_{22}H_{16}F_2N_4O$: C, 67.69; H, 4.13; N, 14.35; Found: C, 67.78; H, 3.96; N, 15.02.

Example 6

3,3-Bis(4-fluorophenyl)-2-(5-phenyl-1H-tetrazol-1-yl)-2-propenal

To a solution of 3.2 g (8.2 mmoles) of 3,3-bis(4-fluorophenyl)-2-(5-phenyl-1H-tetrazol-1-yl)-2-propenol in 200 mL of dry methylene chloride at room temperature was added 1.9 g (8.8 mmoles) of pulverized pyridinium chlorochromate in a single portion. The oxidation was allowed to proceed at room temperature for 24 hours. The crude reaction suspension was diluted with 200 mL of hexanes and the resulting dark brownish suspension was filtered through a bed (1 cm thick) of fine silica gel. The pale filtrate was collected and evaporated under reduced pressure to give the desired product. The solid was recrystallized from an ethyl acetate-hexanes mixture to yield 2.9 g (91.1%) of the title compound; m.p.=193.0°–194.5° C.

Anal. Calcd. for $C_{22}H_{14}F_2N_4O$: C, 68.03; H, 3.63; N, 14.43; Found: C, 68.04; H, 3.61; N, 14.46.

Example 7

5,5-Bis(4-fluorophenyl)-4-(5-phenyl-1H-tetrazol-1-yl)-2,4-pentadienal

To a suspension of 2.8 g (7.2 mmoles) of 3,3-bis(4-fluorophenyl)-2-(5-phenyl-1H-tetrazol-1-yl)-2-propenal in 200 mL of dry (molecular sieves) benzene was added 2.3 g (7.6 mmoles) of triphenylphosphoranylidene acetaldehyde in a single portion and the suspension was heated to reflux temperature for 30 minutes. The crude reaction solution was diluted with hexanes (200 mL) and the suspension was filtered through a bed of silica gel (1 cm thick). Evaporation of the filtrate under reduced pressure gave product which was recrystallized from a mixture of ethyl acetate-hexanes to yield 1.7 g (58%) of the title compound; m.p.=197.5°–199.7° C.

Anal. Calcd. for $C_{24}H_{16}F_2N_4O$: C, 69.56; H, 3.89; N, 13.52; Found: C, 69.63; H, 3.90; N, 13.42.

Example 8

Ethyl 9,9-bis(4-fluorophenyl)-5-hydroxy-8-(5-phenyl-1H-tetrazol-1-yl)-3-oxo-6,8-nonadienoate The dianion of ethyl acetoacetate was generated by adding 0.93 mL (7.3 mmoles) of purified ethyl acetoacetate to a suspension of 0.29 g (60% by weight in oil suspension, 7.3 mmoles) of sodium hydride in tetrahydrofuran (10 mL) at 0° C. under argon followed by the addition of 2.93 mL (7.3 mmoles) of 2.5M n-butyllithium. The orange solution was stirred at 0° C. for one hour then cooled to −80° C. (dry ice-acetone). The dianion solution was added to a solution of 1.01 g (2.4 mmoles) of 5,5-bis(4-fluorophenyl)-4-(5-phenyl-1H-tetrazol-1-yl)-2,4-pentadienal in 20 mL of tetrahydrofuran at −80° C. under argon. After stirring for 10 minutes, the mixture was neutralized with 4 mL of 2M HCl and 4 mL of saturated aqueous NH$_4$Cl solution. The desired product was extracted with ethyl acetate and purified by silica gel column chromatography using a gradient elution of ethyl acetate-hexanes to yield 0.90 g (68%) of the title compound.

$^1$H NMR (CDCl$_3$) δ: 7.3–7.5 (m, 5H), 7.0–7.2 (m, 4H), 6.84 (t, 1H), 6.6 (t, 2H), 6.25 (m, 2H), 5.4 (dt, 1H), 4.7 (br, 1H), 4.15 (dq, 2H), 3.4 (d, 2H), 2.95 (dd, 1H), 2.7 (br, m, 2H), 1.25 (dt, 3H).

Example 9

Ethyl 9,9-bis(4-fluorophenyl)-3,5-dihydroxy-8-(5-phenyl-1H-tetrazol-1-yl)-6,8-nonadienoate A solution containing 0.9 g (1.7 mmoles) of ethyl 9,9-bis(4-fluorophenyl)-5-hydroxy-8-(5-phenyl-1H-tetrazol-1-yl)-3-oxo-6,8-nonadienoate in 20 mL of dry tetrahydrofuran at 0° C. under argon was treated with triethylborane (1.74 mL, 1.0M in THF, 1.74 mmoles). The colorless solution was allowed to stir at 0° C. for 1.5 hours then cooled to −80° C. under argon. To this stirring solution was added sodium borohydride (130 mg, 3.4 mmoles) in one portion and the suspension was stirred for one hour. The crude reaction was quenched with 4.0 mL of 2M HCl followed by 20 mL of half saturated aqueous NH$_4$Cl solution. The mixture was extracted twice with ethyl acetate (40 mL) and the organic layers were combined and evaporated. The concentrated crude product was diluted with 250 mL of methanol and the solution was allowed to stand at room temperature for 45 minutes then concentrated under reduced pressure at room temperature. Analytical TLC showed only one spot for the product. A solution of the crude product was filtered through silica gel and the filtrate was then concentrated under reduced pressure. Recrystallization from a mixture of ethyl acetate-hexanes gave 0.9 g of the title compound; m.p.=160.5°–161.5° C.

Anal. Calcd. for $C_{30}H_{28}F_2N_4O_4$: C, 65.93; H, 5.16; N, 10.25; Found: C, 66.11; H, 5.22; N, 10.26.

Example 10

Sodium 9,9-bis(4-fluorophenyl)-3,5-dihydroxy-8-(5-phenyl-1H-tetrazol-1-yl)-6,8-nonadienoate To a solution of 84.6 mg (0.15 mmole) of ethyl 9,9-bis-(4-fluorophenyl)-3,5-dihydroxy-8-(5-phenyl-1H-tetrazol-1-yl)-6,8-nonadianoate in 10 mL of tetrahydrofuran at 0° C. under argon was added 155 mL of 1.0N NaOH solution and the clear solution was stirred at 0° C. for 4 hours. The saponification was essentially complete as ascertained by analytical TLC. Most of the solvent was evaporated at room temperature under reduced pressure. The residue was diluted with water and lyophilized under high vacuum to give a quantitative yield of the title compound as a fluffy powder.

Anal. Calcd. for $C_{28}H_{23}F_2N_4O_4Na$: C, 62.22; H, 4.29; N, 10.37; Found: C, 61.40; H, 4.50; N, 9.73, H$_2$O, 4.35 (KF).

$^1$H NMR (DMSO-d$_6$) δ: 7.4–7.6 (m, 5H), 7.2–7.4 (m, 4H), 7.0–7.2 (br s, 1H), 6.8–6.9 (t, 2H), 6.6–6.7 (dd, 1H), 6.2–6.3 (dd, 2H), 5.4–5.5 (dd, 1H), 5.3 (br s, 1H), 4.2 (br t, 1H), 3.65 (q, 1H), 2.0 (dd, 1H), 1.8 (dd, 1H), 1.5 (m, 1H), 1.3 (m, 1H).

Example 11

2-Methyl-5-oxo-4,5-dihydro-1,3-oxazole

The title azlactone was prepared by the general procedure described by A. K. Mukerjec, *Heterocycles*, 26(4), 1077 (1987) and was used in the next step without further purification.

Example 12

4-[Bis(4-fluorophenyl)methylene]-3-methyl-5-(4H-oxazolone)

The general procedure of Example 2 was repeated, except that the 2-phenyl-5-oxo-4,5-dihydro-1,3-oxazole utilized therein was replaced by 43 mmoles of 2-methyl-5-oxo-4,5-dihydro-1,3-oxazole [prepared in Example 11] and the product which was thereby produced was recrystallized from benzene-hexanes-ethyl acetate to give 5.4 g (54%) of the title compound; m.p.=135.5°–137.3° C.

Anal. Calcd. for $C_{17}H_{11}F_2NO_2$: C, 68.23; H, 3.70; N, 4.68; Found: C, 68.21; H, 3.69; N, 4.50.

Example 13

Ethyl 3,3-bis(4-fluorophenyl)-2-(acetylamino)-2-propenoate

The general procedure of Example 3 was repeated, except that the 4-[bis(4-fluorophenyl)methylene]-3-phenyl-5-(4H-oxazolone) utilized therein was replaced by 5.1 g of 4-[bis(4-fluorophenyl)methylene]-3-methyl-5-(4H-oxazolone) and the product which was thereby produced was crystallized from ethyl acetate-hexanes to give 5.6 g of the title compound; m.p.=199.7°-200.9° C.

Anal. Calcd. for $C_{19}H_{17}F_2NO_3$: C, 66.08; H, 4.96; N, 4.06; Found: C, 65.85; H, 4.92; N, 4.02.

Example 14

Ethyl 3,3-bis(4-fluorophenyl)-2-(5-methyl-1H-tetrazol-1-yl)-2-propenoate

To a suspension of 5.54 g (16.1 mmoles) of ethyl 3,3-bis(4-fluorophenyl)-2-(acetylamino)-2-propenoate and 9.3 g of triphenylphosphine in 120 mL of dry acetonitrile at room temperature was added dropwise 6.82 mL of carbon tetrachloride. The pale suspension was stirred for 45 minutes. To this clear orange solution was added 2.3 g of sodium azide and 0.6 g of tetra n-butyl ammonium bromide and stirring was continued. The orange suspension soon became pale with the formation of a white precipitate. After 3 hours, the mixture was filtered and the solution was concentrated under reduced pressure. More triphenylphosphine oxide was removed and the desired product was purified by crystallizations from ethyl acetate-hexanes to give 5.3 g (88%) of the title compound; m.p.=102.9°-103.5° C.

Anal. Calcd. for $C_{19}H_{16}F_2N_4O_2$: C, 61.62; H, 4.35; N, 15.13; Found: C, 61.39; H, 4.36; N, 15.02.

Example 15

3,3-Bis(4-fluorophenyl)-2-(5-methyl-1H-tetrazol-1-yl)-2-propenol

The general procedure of Example 5 was repeated, except that the ethyl 3,3-bis(4-fluorophenyl)-2-(5-phenyl-1H-tetrazol-1-yl)-2-propenoate utilized therein was replaced by 4.87 g of ethyl 3,3-bis(4-fluorophenyl)-2-(5-methyl-1H-tetrazol-1-yl)-2-propenoate [prepared in Example 14] and there was thereby produced 4.45 g of the title compound which was used in the next step without further purification.

Example 16

3,3-Bis(4-fluorophenyl)-2-(5-methyl-1H-tetrazol-1-yl)-2-propenal

The general procedure of Example 6 was repeated, except that the 3,3-bis(4-fluorophenyl)-2-(5-phenyl-1H-tetrazol-1-yl)-2-propenol utilized therein was replaced by 4.45 g of 3,3-bis(4-fluorophenyl)-2-(5-methyl-1H-tetrazol-1-yl)-2-propenol [prepared in Example 15] and there was thereby produced 3.76 g of the title compound which was used in the next step without further purification.

A sample of the product was crystallized from ethyl acetate-hexanes to give pure title compound; m.p.=150.6°-152.5° C.

Example 17

5,5-Bis(4-fluorophenyl)-4-(5-methyl-1H-tetrazol-1-yl)-2,4-pentadienal

Following the general procedure of Example 7, 3.8 g (11.6 mmoles) of 3,3-bis(4-fluorophenyl)-2-(5-methyl-1H-tetrazol-1-yl)-2-propenal in 200 mL of dry benzene was treated with 3.8 g (12.5 mmoles) of triphenylphosphoranylidene acetaldehyde to produce 3.5 g (85%) of the title compound; m.p.=72°-78° C. (foam).

Anal. Calcd. for $C_{19}H_{14}F_2N_4O$: C, 64.77; H, 4.00; N, 15.90; Found: C, 64.92; H, 4.26; N, 14.88.

Example 18

Ethyl 9,9-bis(4-fluorophenyl)-5-hydroxy-8-(5-methyl-1H-tetrazol-1-yl)-3-oxo-6,8-nonadienoate The general procedure of Example 8 was repeated except that the 5,5-bis(4-fluorophenyl)-4-(5-phenyl-1H-tetrazol-1-yl)-2,4-pentadienal utilized therein was replaced by 2.3 g of 5,5-bis(4-fluorophenyl)-4-(5-methyl-1H-tetrazol-1-yl)-2,4-pentadienal and there was thereby produced 2.0 g (64.2%) of the title compound after silica gel column chromatogrphy using ethyl acetate-hexanes as eluent.

$^1H$ NMR (CDCl$_3$) δ: 7.2–7.3 (m, 2H), 7.1 (t, 2H), 6.6–6.85 (m, 5H), 5.0 (dd, 1H), 4.6 (br m, 1H), 4.15 (q, 2H), 3.4 (d, 2H), 2.92 (br s, 1H), 2.6–2.7 (m, 2H), 2.15 (s, 3H), 1.25 (t, 3H).

Example 19

Ethyl 9,9-bis(4-fluorophenyl)-3,5-dihydroxy-8-(5-methyl-1H-tetrazol-1-yl)-6,8-nonadienoate The general procedure of Example 9 was repeated except that the ethyl 9,9-bis(4-fluorophenyl)-5-hydroxy-8-(5-phenyl-1H-tetrazol-1-yl)-3-oxo-6,8-nonadienoate utilized therein was replaced by 2.0 g of 9,9-bis(4-fluorophenyl)-5-hydroxy-8-(5-methyl-1H-tetrazol-1-yl)-3-oxo-6,8-nonadienoate and there was thereby produced 1.25 g (63%) of the title compound after purification by silica gel column chromatography with ethyl acetate in hexanes as eluent.

$^1H$ NMR (CDCl$_3$) δ: 7.2–7.4 (m, 2H), 7.0–7.2 (m, 2H), 6.7–6.9 (m, 4H), 6.6–6.7 (br, 1H), 5.0 (dd, 1H), 4.4 (dd, 1H), 4.2 (dd, 1H), 4.1 (q, 2H), 3.81 (br, 2H, 2-hydroxy OH), 2.41 (d, 2H), 2.17 (s, 3H), 1.53 (m, 2H), 1.24 (t, 3H).

Anal. Calcd. for $C_{25}H_{26}F_2N_4O_4$: C, 61.98; H, 5.41; N, 11.56; Found: C, 62.35; H, 5.71; N, 10.99.

Example 20

Sodium 9,9-bis(4-fluorophenyl)-3,5-dihydroxy-8-(5-methyl-1H-tetrazol-1-yl-6,8-nonadienoate The general saponification procedure of Example 10 was followed except that 95.9 mg of ethyl 9,9-bis(4-fluorophenyl)-3,5-dihydroxy-8-(5-methyl-1H-tetrazol-1-yl)-6,8-nonadienoate was utilized therein to produce the title compound in quantitative yield.

Anal. Calcd. for $C_{23}H_{21}F_2N_4O_4Na$: C, 57.74; H, 4.42; N, 11.71; Found: C, 56.36; H, 4.77; N, 10.76; H$_2$O, 3.78 (KF)

$^1H$ NMR (DMSO-d$_6$) δ: 7.3–7.4 (m, 4H), 7.05 (t, 2H), 6.8–6.9 (m, 2H), 6.5 (d, 1H), 5.2 (br s, 1H), 5.0 (dd, 1H), 4.17 (dd, 1H), 3.63 (m, 1H), 3.4 (br s, 1H), 2.27 (s, 3H), 2.0 (dd, 1H), 1.8 (dd, 1H), 1.45 (m, 1H), 1.26 (m, 1H).

Example 21

Ethyl 3,3-bis(4-fluorophenyl)-2-formylamino-2-propenoate

To a chilled (0° C., ice-bath) stirring mixture of 3.2 g (14.7 mmoles) of 4,4'-difluorobenzophenone and 2 mL (18.3 mmoles) of ethyl isocyanoacetate in 30 mL of dry tetrahydrofuran was added 1.03 g (60% suspension, 25.7 mmoles) of sodium hydride in one portion. The reaction was very vigorous at the beginning and the color became dark brownish. The mixture was allowed to stir at 0° C. for one hour then allowed to warm to room temperature and continued for 24 hours. The crude reaction mixture was quenched with 30 mL of saturated aqueous NH$_4$Cl solution and the product was extracted twice with ethyl acetate (40 mL). The organic layers were combined, dried over MgSO$_4$ and evaporated to dryness. The desired product was recrystallized from a mixture of ethyl acetate-hexanes to yield 3.7 g (80.4%) of the title compound; m.p.=174.1°–175.7° C.

Anal. Calcd. for C$_{18}$H$_{15}$F$_2$NO$_3$: C, 65.25; H, 4.56; N, 4.23; Found: C, 65.21; H, 4.51; N, 4.28.

Example 22

Ethyl α-[bis(4-fluorophenyl)methylene]-1H-tetrazole-1-acetate

A. Ethyl 3,3-bis(4-fluorophenyl)-2-isocyano-2-propenoate

To a chilled (0° C., ice-bath) mixture of 5.0 g (15.1 mmoles) of ethyl 3,3-bis(4-fluorophenyl)-2-formylamino-2-propenoate and 8.4 mL (60.7 mmoles) of triethylamine in 150 mL of dry methylene chloride under argon was added dropwise 13 g (32 mmoles, 24% by weight in toluene) of phosgene. Near the end of addition a yellow precipitate was observed and the suspension was stirred for an additional 10 minutes. The isocyano intermediate was used directly in the next step without further purification.

An analytical pure sample of the title compound was obtained by filtration of the crude suspension through a bed of silica gel-H followed by concentration and crystallization from a mixture of ethyl acetate-hexanes; m.p.=92°–95° C. (dec.).

Anal. Calcd. for C$_{18}$H$_{13}$F$_2$NO$_2$: C, 69.01; H, 4.15; N, 4.47; Found: C, 69.09; H, 4.14; N, 4.44.

B. Ethyl α-[bis(4-fluorophenyl)methylene]-1H-tetrazole-1-acetate

To a crude reaction mixture from Step A was added 2 g (31 mmoles) of pulverized sodium azide, and 0.6 g (1.9 mmole) of tetra n-butyl ammonium bromide. The mixture was stirred at reflux temperature for a total of four days. Analytical TLC showed both isocyano intermediate and desired product. The crude reaction mixture was filtered through a bed of silica gel and the filtrate was evaporated. The residue was dissolved in 200 mL of ethyl acetate, washed with 1N HCl, dried over MgSO$_4$ and concentrated under reduced pressure. The crude product was further purified by silica gel chromatography to give 3 g of the N-formyl starting material and 1.4 g (25%) of the desired tetrazole product. Recrystallization from ethyl acetate-hexanes gave the title compound; m.p.=117.8°–119.2° C.

Anal. Calcd. for C$_{18}$H$_{14}$F$_2$N$_4$O$_2$: C, 60.67; H, 3.96; N, 15.72; Found: C, 60.65; H, 3.89; N, 15.82.

$^1$H NMR (CDCl$_3$) δ: 8.33 (s, 1H), 7.15–7.25 (m, 2H), 7.05–7.15 (m, 2H), 6.82–6.91 (m, 4H), 4.06 (q, 2H), 0.97 (t, 3H).

$^{13}$C NMR (CDCl$_3$) δ: 144.02 (tetrazole carbon).

Example 23

3,3-Bis(4-fluorophenyl)-2-(1H-tetrazol-1-yl)-2-propenol

A. 3,3-Bis(4-fluorophenyl)-2-(1H-tetrazol-1-yl)-2-propenoic acid

The saponification was performed by the addition of 1.14 mL of 2.0M LiOH solution to a solution of 0.27 g (0.76 mmole) of ethyl α-[bis(4-fluorophenyl)methylene]-1H-tetrazole-1-acetate in 5 mL of 95% ethanol at room temperature. After two hours, the crude reaction mixture was diluted with water and washed with diethyl ether (20 mL×2). The free acid in the aqueous layer was regenerated by the addition of aqueous HCl then extracted with diethyl ether, dried and evaporated. The crude acid was dried under high vacuum for 48 hours before it was used in the next step.

$^1$H NMR (CDCl$_3$) δ: 8.4 (s, 1H), 7.0–7.1 (m, 2H), 6.8–6.9 (m, 2H), 6.6–6.7 (dd, 4H).

B. 3,3-Bis(4-fluorophenyl)-2-(1H-tetrazol-1-yl)-2-propenol

The crude acid from Step A was suspended in 12 mL of dry benzene and the mixture was treated with 350 mL of oxalyl chloride. To this suspension was added one drop of pyridine and a very vigorous reaction was apparent. The clear homogenous solution was warmed to reflux temperature for 10 minutes then kept at about 70° C. for 2 days under an argon atmosphere. Most of the solvents were evaporated under high vacuum and the semi-solid was dissolved in 6 mL of tetrahydrofuran. To this chilled (−80° C., dry ice-acetone) solution under argon was added dropwise 0.5 mL (0.5 mmole, 1.0M in tetrahydrofuran) of lithium aluminum hydride and the reduction was complete in one hour. The crude reaction mixture was quenched with 2.0M HCl and the organic residue was extracted with ethyl acetate, dried and evaporated to give 0.21 g (88.7%) of the title compound which was pure enough to be used in the next step.

An analytical pure sample of the title compound was obtained by silica gel column chromatography followed by recrystallizations from ethyl acetate-hexanes; m.p.=152°–154° C.

Anal. Calcd. for C$_{16}$H$_{12}$F$_2$N$_4$O: C, 61.14; H, 3.85; N, 17.85; Found: C, 60.84; H, 3.83; N, 17.77.

Example 24

3,3-Bis(4-fluorophenyl)-2-(1H-tetrazol-1-yl)-2-propenal

Following the general procedure of Example 6, 0.21 g (0.67 mmole) of 3,3-bis(4-fluorophenyl)-2-(1H-tetrazol-1-yl)-2-propenol was treated with 288 mg (1.33 mmoles) of pyridinium chlorochromate in 10 mL of methylene chloride and there was thereby produced 117 mg (56%) of the title compound after crystallization from ethyl acetate-hexanes; m.p. 160.7°–161.4° C.

Anal. Calcd. for C$_{16}$H$_{10}$F$_2$N$_4$O: C, 61.54; H, 3.23; N, 17.94; Found: C, 61.59; H, 3.26; N, 18.13.

Example 25

5,5-Bis(4-fluorophenyl)-4-(1H-tetrazol-1-yl)-2,4-pentadienal

The reaction was carried out following the general procedure described in Example 7. A suspension of 224.4 mg (0.72 mmole) of 3,3-bis(4-fluorophenyl)-2-(1H-tetrazol-1-yl)-2-propenal and 220 mg (0.72 mmole) of triphenylphosphoranylidene acetaldehyde in 38 mL of dry benzene was stirred at room temperature for 16 hours. The crude reaction mixture was chromatographed on a silica gel column and the purified product thereby obtained was recrystallized from ethyl acetate-hexanes to give 194 mg (92%) of the title compound; m.p.=152.2°–153.7° C.

Anal. Calcd. for C$_{18}$H$_{12}$F$_2$N$_4$O: C, 63.90; H, 3.57; N, 16.56; Found: C, 63.87; H, 3.64; N, 16.37.

Example 26

Ethyl 9,9-bis(4-fluorophenyl)-5-hydroxy-8-(1H-tetrazol-1-yl)-3-oxo-6,8-nonadienoate Following the general procedure of Example 8, 196 mg (0.58 mmole) of 5,5-bis(4-fluorophenyl)-4-(1H-tetrazol-1-yl)-2,4-pentadienal was condensed with two equivalents (1.2 mmoles) of the dianion of ethyl acetoacetate. The product thereby produced was purified by silica gel chromatography using ethyl acetate-hexanes as eluent to yield 173.8 mg (61.5%) of the title compound.

$^1$H NMR (CDCl$_3$) δ: 8.16 (s, 1H), 7.01–7.12 (m, 3H), 6.96 (t, 2H), 6.53–6.70 (m, 4H), 4.96 (dd, 1H), 4.47 (br m, 1H), 4.00 (q, 2H), 2.79 (d, 1H), 3.26 (s, 2H), 2.46–2.62 (m, 2H), 1.09 (s, 3H).

Example 27

Ethyl 9,9-bis(4-fluorophenyl)-3,5-dihydroxy-8-(1H-tetrazol-1-yl)-6,8-nonadienoate The reduction was carried out following the procedure described in Example 9. A solution of 180 mg (0.38 mmole) of ethyl 9,9-bis(4-fluorophenyl)-5-hydroxy-8-(1H-tetrazol-1-yl)-3-oxo-6,8-nonadienoate in 10 mL of tetrahydrofuran at 0° C. was treated with triethylborane (0.9 mL, 1M in tetrahydrofuran). After 2 hrs., the solution was cooled to −80° C. and treated with 30 mg of sodium borohydride followed by 200 μL of methanol. The crude product was purified by silica gel chromatography to yield 111.2 mg (62%) of the title compound.

$^1$H NMR (CDCl$_3$) δ: 8.36 (s, 1H), 7.29–7.34 (m, 2H), 7.17 (t, 2H), 6.77–6.92 (m, 5H), 5.21 (dd, 1H), 4.51 (m, 1H), 4.25 (m, 1H), 4.21 (q, 2H and m, 1H), 3.77 (br m, 1H), 2.49 (d, 2H), 1.59 (m, 2H), 1.31 (t, 3H).

Example 28

9,9-Bis(4-fluorophenyl)-3,5-dihydroxy-8-(1H-tetrazol-1-yl)-6,8-nonadienoic acid, sodium salt The saponification of 111.6 mg (0.23 mmole) of ethyl 9,9-bis(4-fluorophenyl)-3,5-dihydroxy-8-(1H-tetrazol-1-yl)-6,8-nonadienoate in 2.0 mL of tetrahydrofuran at 0° C. under argon with 237 μL of 1.0M aqueous sodium hydroxide was carried out following the general procedure of Example 10. The title compound was obtained in quantitative yield.

MS (FAB): m/e=464 for (M+H)$^+$;

Anal. Calcd. for C$_{22}$H$_{19}$F$_2$N$_4$O$_4$Na.0.5H$_2$O C, 55.82; H, 4.26; N, 11.83; Found: C, 56.14; H, 4.55; N, 10.62.

$^1$H NMR (DMSO-d$_6$) δ: 9.70 (s, 1H), 7.48–7.57 (m, 4H), 7.27 (br s, 1H), 7.19 (t, 2H), 7.05–7.10 (m, 2H), 6.73 (d, 1H), 5.36 (br s, 1H), 5.24 (dd, 1H), 4.36 (br q, 1H), 3.80 (br q, 1H), 2.18 (dd, 1H), 2.00 (dd, 1H), 1.63 (m, 1H), 1.42 (m, 1H).

Example 29

3,3-Bis(4-fluorophenyl)-1-bromo-2-(1H-tetrazol-1-yl)-2-propene

A solution of 3,3-bis(4-fluorophenyl)-2-(tetrazol-1-yl)-2-propenol (108 mg, 0.34 mmol), triphenylphosphine (118 mg, 0.45 mmol) and N-bromosuccinimide (74 mg, 0.42 mmol) in tetrahydrofuran (5 mL) was stirred in an inert atmosphere for a period of 1.5 hours. The suspension (triphenylphosphine oxide precipitate) was diluted with hexanes (25 mL) and the suspension was filtered. The filtrate was concentrated under reduced pressure and the semi-crystalline solid was filtered through a short silica gel column eluted with 5–10% ethyl acetate in hexanes. The title compound, 108 mg (84%), was obtained after removal of solvents under reduced pressure.

$^1$H NMR (CDCl$_3$) δ: 8.185 (s, 1H), 7.42 (m, 2H), 7.156 (m, 2H), 6.82 (m, 4H), 4.488 (s, 2H).

Example 30

Dimethyl [3,3-bis(4-fluorophenyl)-2-(1H-tetrazol-1-yl)-2-propen-1-yl]phosphonate A suspension of 3,3-bis(4-fluorophenyl)-1-bromo-2-(tetrazol-1-yl)-2-propene (108 mg, 0.29 mmol) and trimethylphosphite (4 mL, 34 mmol) was heated to reflux under an inert atmosphere for five minutes. After cooling to room temperature, excess trimethylphosphite was evaporated under reduced pressure to give a pale crystalline material. The crude product was crystallized from a 10:1 mixture of hexanes: ethyl acetate to give 98 mg (83%) of the title compound as rhombic, colorless crystals; m.p.=132.8°–133.7° C.

$^1$H NMR (CDCl$_3$) δ: 8.184 (s, 1H), 7.46 (m, 2H), 7.112 (m, 2H), 8.82 (m, 4H), 3.537 (s, 3H), 3.5 (s, 3H), 3.342 (d, 2H, J=21.3 Hz).

Example 31

Cis-2,2-dimethyl-6-(2-phenylethenyl)-1,3-dioxane-4-acetic acid methyl ester

Methyl 3,5-dihydroxy-7-phenyl-6-enoate (98% diastereomeric purity) (2.37 g, 9.48 mmol) was stirred with 2,2-dimethoxypropane (20 mL) and a catalytic amount of p-toluenesulfonic acid for 16 hours. The solution was partitioned between diethyl ether and dilute aqueous sodium bicarbonate solution. The organic layer was dried (Na$_2$SO$_4$) and concentrated under reduced pressure to afford a yellow solid. After recrystallization from isopropyl ether, 1.70 g (62%) of the title compound was obtained as a white solid; m.p.=84°–86.5° C.

Alternatively, 0.2 g of solid sodium carbonate can be added to the 2,2-dimethoxypropane solution and the solution stirred vigorously. The solid is filtered through a fluted filter paper. The excess 2,2-dimethoxypropane is removed under reduced pressure to afford a yellow solid which is recrystallized from isopropyl ether.

$^1$H NMR (CDCl$_3$) δ: 7.37–7.19 (5H, m), 6.59 (1H, d, J=15.9 Hz), 6.14 (1H, dd, J=15.9, 6.4 Hz), 4.57–4.35 (1H, m), 4.42–4.35 (1H, m), 3.68 (3H, s), 2.58 (1H, d, J=15.6, 6.9 Hz), 2.14 (1H, dd, J=15.6, 6.3 Hz), 1.74–1.61 (1H, m), 1.52 (3H, s), 1.43 (3H, s), 1.45–1.35 (1H, m).

Anal. Calcd. for C$_{17}$H$_{22}$O$_4$: C, 70.32; H, 7.63; Found: C, 70.24; H, 7.69.

Example 32

Cis-2,2-dimethyl-6-(2-phenylethenyl)-1,3-dioxane-4-acetic acid

A solution of 2,2-dimethyl-6-(2-phenylethenyl)-1,3-dioxane-4-acetic acid methyl ester (8.5 g, 29.3, mmol) in 1N NaOH (32 mL) and methanol (64 mL) was heated to reflux for 45 minutes. After evaporation under reduced pressure, the aqueous solution was washed once with diethyl ether and acidified with 1N HCl (33 mL). The precipitate was collected and recrystallized from ethyl acetate/isopropyl ether to afford 7.2 g (90%) of the title compound as a colorless solid; m.p.=153°–155° C.

$^1$H NMR (CDCl$_3$) δ: 7.37–7.20 (5H, m), 6.60 (1H, d, J=16.0 Hz), 6.14 (1H, dd, J=16.0, 6.4 Hz), 4.59–4.54 (1H, m), 4.43–4.35 (1H, m), 2.62 (1H, dd, J=16.0, 7.2 Hz), 2.51 (1H, dd, J=16.0, 5.3 Hz), 1.77–1.72 (1H, m), 1.54 (3H, s), 1.46 (3H, s), 1.50–1.36 (1H, m).

Anal. Calcd. for C$_{16}$H$_{20}$O$_4$: C, 69.54; H, 7.30; Found: C, 69.20; H, 7.33.

Example 33

Resolution of cis-2,2-dimethyl-6-(2-phenylethenyl)-1,3-dioxane-4-acetic acid

The racemic cis-2,2-dimethyl-6-(2-phenylethenyl)-1,3-dioxane-4-acetic acid (0.31 g, 1.1 mmol) (prepared in Example 32) was dissolved in a boiling solution of hexane/ethanol containing (1S,2R)-ephedrine (0.2 g, 1.1 mmol). The resulting solution was very slowly brought to room temperature to give 0.21 g (41.4%) of colorless chiral salt (the usage of diastereomerically pure seed crystal is recommended during the resolution): m.p.=170°-171° C.

The chiral acid was freed through an acidic workup (as described in Example 4) and its enantiomeric purity was determined to be 100% by $^1$H NMR using L-phenyltrifluoromethyl carbinol as a chiral solvent. $[\alpha]_D^{25}=+5.45°$ (c=1, CHCl$_3$).

Example 34

Cis-(4R,6S)-2,2-dimethyl-6-formyl-1,3-dioxane-4-acetic acid

The resolved salt of cis-2,2-dimethyl-6-(2-phenylethenyl)-1,3-dioxane-4-acetic acid and (1S,2R)-ephedrine (6.6 g, 14.9 mmol) (prepared in Example 33) was partitioned between 0.5N HCl (30 mL) and diethyl ether. The ether layer was washed with brine, dried (MgSO$_4$/Na$_2$SO$_4$), and concentrated under reduced pressure to afford 4.1 g (99.6%) of the free acid. This acid was dissolved in dry methylene chloride (100 mL) and ozone was passed through this solution at −78° C. until there was deep blue coloration. Excess ozone was removed by purging with nitrogen and the ozonide formed was decomposed by adding CH$_3$SCH$_3$ (5 mL) and warming the solution to room temperature and allowed to stand for 16 hours. The solution was concentrated under reduced pressure and the residue was dissolved in isoamyl ether (ca 100 mL). The benzaldehyde which was formed during the ozonolysis was azeotroped together with isoamyl ether under reduced pressure to afford the title compound.

$^1$H NMR (CDCl$_3$) δ: 9.57 (1H, s), 4.40–4.30 (2H, m), 2.60 (1H, dd, J=16.0, 7.0 Hz), 2.49 (1H, dd, J=16.0, 6.0 Hz), 1.88–1.83 (1H, m), 1.49 (3H, s), 1.46 (3H, s), 1.42–1.31 (1H, m).

Example 35

(3R, 5S)-9,9-Bis(4-fluorophenyl)-3,5-dihydroxy-8-(1H-tetrazol-1-yl)-6,8-nonadienoic acid When a suspension of the lithium salt of the crude chiral acid prepared in Example 34 is treated with the phosphonate anion of dimethyl[3,3-bis(4-fluorophenyl)-2-(1H-tetrazol-1-yl)-2-propen-1-yl]phosphonate generated with n-BuLi in THF at about −78° C. and the product thereof is treated with 0.2N HCl there is thereby produced the title compound.

Example 36

Methyl 2,2-dimethyl-6-formyl-1,3-dioxane-4-acetate

Cis-2,2-dimethyl-6-(2-phenylethenyl)-1,3-dioxane-4-acetic acid methyl ester (prepared in Example 31) was dissolved in methanol (10 mL) and ozone was passed through the solution at −78° C. until the color of the solution turned blue. The reaction mixture was purged with nitrogen to remove excess ozone then dimethyl sulfide was added and the temperature was allowed to warm up to room temperature. The reaction was evaporated in vacuo and the residual oil was purified by chromatography on silica gel using diethyl ether-hexane (3:1) as the eluent to afford the title compound.

$^1$H NMR (360 MHz, CDCl$_3$) δ: 9.53 (1H, s), 4.40–4.23 (2H, m), 3.69 (3H, s), 2.53 (1H, dd, J=15.8, 7.02 Hz), 2.37 (1H, dd, J=15.8, 5.98 Hz), 1.85–1.76 (1H, m), 1.44 (3H, s), 1.40 (3H, s), 1.35–1.23 (1H, m).

Example 37

Erythro-9,9-bis(4-fluorophenyl)-3,5-dihydroxy-8-(1H-tetrazol-1-yl)-6,8-nonadienoic acid When a solution of the formyl ester prepared in Example 36 is treated with the phosphonate anion of dimethyl[3,3-bis(4-fluorophenyl)-2-(1H-tetrazol-1-yl)-2-propen-1-yl]phosphonate generated with n-BuLi in THF at about −78° C. and the product thereof is deprotected and hydrolyzed with 0.2N HCl and sodium hydroxide there is thereby produced the title compound.

Example 38

1,1-Dimethylethyl 2,2-dimethyl-6-(2-phenylethenyl)-1,3-dioxane-4-acetate

To a solution of 1,1-dimethylethyl 3,5-dihydroxy-7-phenyl-6-heptenoate (5.5 g, 19 mmol) in acetone (2.3 g, 40 mmol) was added a catalyic amount of p-toluenesulfonic acid. After stirring for 2 hours, the mixture had solidified and was dissolved in excess acetone and filtered through a pad of sodium carbonate. The excess acetone was removed in vacuo and the residue crystallized from isopropyl ether to give 3.4 g of the title compound; m.p.=91°–93° C.

Anal. Calcd. for C$_{20}$H$_{28}$O$_4$: C, 72.27; H, 8.50; Found: C, 71.98; H, 8.91.

Example 39

1,1-Dimethylethyl 6-formyl-2,2-dimethyl-1,3-dioxane-4-acetate

Ozone was bubbled into a solution of 1,1-dimethylethyl 2,2-dimethyl-6-(2-phenylethenyl)-1,3-dioxane-4-acetate (3.0 g, 9 mmol) in 100 mL of methylene chloride at −78° C. until a blue color persisted. Nitrogen was then bubbled into the solution without cooling until the color disappeared. The temperature had risen to −20° C. Methyl sulfide (3 mL) was added and the solution stirred for 18 hours. The solvent was removed in vacuo and the residue purified by chromatography on silica eluting with 20% ethyl acetate in hexane to give 1.78 g of the title compound. Recrystallization from pentane gave the compound as a white solid; m.p.=71°–73° C.

Anal. Calcd. for C$_{13}$H$_{22}$O$_5$: C, 60.45; H, 8.59; Found: C, 60.28; H, 8.64.

What is claimed is:

1. A compound of the formula

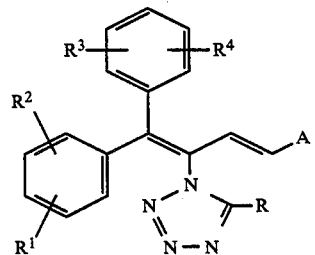

wherein
R$^1$, R$^2$, R$^3$ and R$^4$ each are independently hydrogen, halogen, C$_{1-4}$alkyl, C$_{1-4}$alkoxy, or trifluoromethyl;
R is hydrogen, C$_{1-4}$alkyl or phenyl;
A is

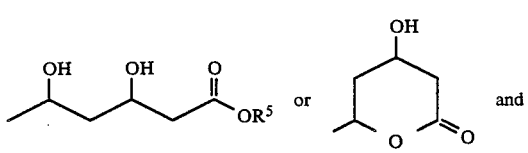

$R^5$ is hydrogen, a hydrolyzable ester group or a cation to form a non-toxic pharmaceutically acceptable salt.

2. A compound of claim 1 having the formula

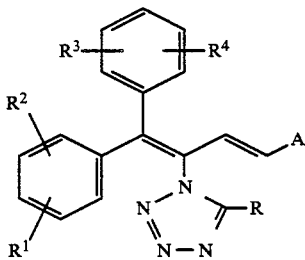

wherein $R^1$, $R^2$, $R^3$ and $R^4$ each are independently hydrogen, fluoro, chloro or methyl;

R is hydrogen, $C_{1-4}$alkyl or phenyl;

A is

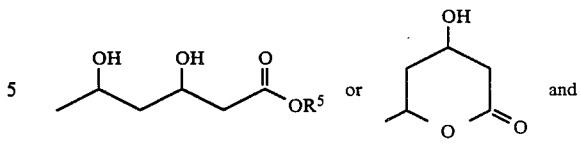

$R^5$ is hydrogen, a hydrolyzable ester group or a cation to form a non-toxic pharmaceutically acceptable salt.

3. A compound of claim 2 wherein R is hydrogen.
4. A compound of claim 2 wherein R is methyl.
5. A compound of claim 2 wherein R is phenyl.
6. The compound of claim 3 which is 9,9-bis(4-fluorophenyl)-3,5-dihydroxy-8-(1H-tetrazol-1-yl)-6,8-nonadienoic acid or a nontoxic pharmaceutically acceptable salt.
7. The compound of claim 6 which is the (3R, 5S) enantiomer of 9,9-bis(4-fluorophenyl)-3,5-dihydroxy-8-(1H-tetrazol-1-yl)-6,8-nonadienoic acid or a non-toxic pharmaceutically acceptable salt.
8. The compound of claim 3 which is trans-6-[4,4-bis(4-fluorophenyl)-3-(1H-tetrazol-1-yl)-1,3-butadienyl]-tetrahydro-4-hydroxy-2H-pyran-2-one.
9. The compound of claim 8 which is the (4R, 6S) enantiomer of 6-[4,4-bis(4-fluorophenyl)-3-(1H-tetrazol-1-yl)-1,3-butadienyl]-tetrahydro-4-hydroxy-2H-pyran-2-one.
10. The compound of claim 4 which is 9,9-bis(4-fluorophenyl)-3,5-dihydroxy-8-(5-methyl-1H-tetrazol-1-yl)-6,8-nonadienoic acid or a non-toxic pharmaceutically acceptable salt.
11. The compound of claim 4 which is trans-6-[4,4-bis(4-fluorophenyl)-3-(5-methyl-1H-tetrazol-1-yl)-1,3-butadienyl]-tetrahydro-4-hydroxy-2H-pyran-2-one.

* * * * *